US008135468B2

(12) United States Patent
Gutfinger et al.

(10) Patent No.: US 8,135,468 B2
(45) Date of Patent: Mar. 13, 2012

(54) SYSTEMS AND METHODS FOR ESTIMATING LEFT ATRIAL PRESSURE (LAP) IN PATIENTS WITH ACUTE MITRAL VALVE REGURGITATION FOR USE BY AN IMPLANTABLE MEDICAL DEVICE

(75) Inventors: Dan E. Gutfinger, Agoura Hills, CA (US); Fujian Qu, Sunnyvale, CA (US); Alex Soriano, Ventura, CA (US); Ryan Rooke, Redondo Beach, CA (US); Yelena Nabutovsky, Sunnyvale, CA (US); Riddhi Shah, Mountain View, CA (US)

(73) Assignee: Pacesetter, Inc., Sylmar, CA (US)

( * ) Notice: Subject to any disclaimer, the term of this patent is extended or adjusted under 35 U.S.C. 154(b) by 108 days.

(21) Appl. No.: 12/853,157

(22) Filed: Aug. 9, 2010

(65) Prior Publication Data

US 2012/0035681 A1 Feb. 9, 2012

(51) Int. Cl.
*A61N 1/00* (2006.01)

(52) U.S. Cl. ......................................................... 607/28
(58) Field of Classification Search ...................... 607/28
See application file for complete search history.

(56) References Cited

U.S. PATENT DOCUMENTS

| | | | |
|---|---|---|---|
| 4,674,518 A | 6/1987 | Salo | |
| 6,249,705 B1 | 6/2001 | Snell | |
| 6,328,699 B1 | 12/2001 | Eigler et al. | |
| 6,438,408 B1 | 8/2002 | Mulligan et al. | |
| 6,480,733 B1 | 11/2002 | Turcott | |
| 6,512,949 B1 | 1/2003 | Combs et al. | |
| 6,512,952 B2 | 1/2003 | Stahmann et al. | |
| 6,572,557 B2 | 6/2003 | Tchou et al. | |
| 6,628,988 B2 | 9/2003 | Kramer et al. | |
| 6,643,546 B2 | 11/2003 | Mathis et al. | |
| 6,643,548 B1 | 11/2003 | Mai et al. | |
| 6,645,153 B2 | 11/2003 | Kroll et al. | |
| 6,741,885 B1 | 5/2004 | Park et al. | |
| 6,748,261 B1 | 6/2004 | Kroll et al. | |
| 6,829,503 B2 | 12/2004 | Alt | |
| 6,970,742 B2 | 11/2005 | Mann et al. | |
| 7,115,095 B2 | 10/2006 | Eigler et al. | |
| 7,139,609 B1 | 11/2006 | Min et al. | |
| 7,272,443 B2 | 9/2007 | Min et al. | |
| 7,437,192 B2 | 10/2008 | Gill et al. | |
| 7,483,743 B2 | 1/2009 | Mann et al. | |
| 7,502,644 B2 | 3/2009 | Gill et al. | |

(Continued)

OTHER PUBLICATIONS

Bini, G.C. et al. "A Method to Calculate Tissue Impedance through a Standard Bipolar Pacing Lead," Cardiovasc Eng. 2006;6:45-52.

(Continued)

*Primary Examiner* — George Manuel

(57) ABSTRACT

Various techniques are provided for use with an implantable medical device for estimating cardiac pressure within a patient based on admittance (or related electrical values such as impedance or conductance) that takes into account the presence of acute MR within the patient. Briefly, the device detects an indication of acute MR, if occurring within the patient. The device also applies electrical fields to tissues of the patient and measures electrical parameters influenced by the electrical field, such as admittance, impedance or conductance. The device then estimates cardiac pressure within the patient based on the measured electrical parameter and the indication of acute MR. In one example, different linear correlation functions are used to convert admittance values to left atrial pressure (LAP) values depending upon the presence or absence of acute MR within the patient.

20 Claims, 10 Drawing Sheets

U.S. PATENT DOCUMENTS

| | | | |
|---|---|---|---|
| 7,505,814 B2 | 3/2009 | Bornzin et al. | |
| 7,695,512 B2 * | 4/2010 | Lashinski et al. | 623/2.37 |
| 2008/0262361 A1 | 10/2008 | Gutfinger et al. | |
| 2009/0018597 A1 | 1/2009 | Wenzel et al. | |

OTHER PUBLICATIONS

Braunwald, Eugene MD, "Mitral Regurgitation: Physiological, Clinical and Surgical Considerations," from Seminars in Medicine of the Beth Israel Hospital, Boston, reprinted from N Engl J Med. Aug. 21, 1969; 281:425-433.

Burch, G.E. MD et al, "The syndrome of papillary muscle dysfunction," Am Heart J. 1968;75:399-415.

Cheng, Tsung O. MD, "Some New Observations on the Syndrome of Papillary Muscle Dysfunction," Am J Med. 1969;47:924-945.

De Busk, robert F. MD et al., "The clinical spectrum of papillary muscle disease," in Medical Progress reprinted from N Engl J Med. 1969;281:1458-1467.

Khoury, Dirar S. PhD et al., "Ambulatory Monitoring of Congestive Heart Failure by Multiple Bioelectric Impedance Vectors," J Am Coll Cardiol, 2009; 53(12):1075-1081.

Levine, Robert A. MD et al., "Ischemic Mitral Regurgitation on the Threshold of a Solution From Paradoxes to Unifying Concepts," Circulation. 2005;112:745-758.

Ritzema, Jay MRCP et al. "Physician-Directed Patient Self-Management of Left Atrial Pressure in Advanced Chronic Heart Failure," Circulation. 2010;121:1086-1095.

Schlant, Robert C. MD, "The Management of Chronic Mitral Regurgitation," Council on Clinical Cardiology Newletter, editted by Beller. 1986;12(1)::1-9.

* cited by examiner

SYSTEMS AND METHODS FOR ESTIMATING LEFT ATRIAL PRESSURE (LAP) IN PATIENTS WITH ACUTE MITRAL VALVE REGURGITATION FOR USE BY AN IMPLANTABLE MEDICAL DEVICE

CROSS REFERENCE TO RELATED APPLICATIONS

This application is related to U.S. patent application Ser. No. 12/853,130 filed concurrently herewith, titled "Near Field-Based Systems and Methods for Assessing Impedance and Admittance for Use with an Implantable Medical Device".

FIELD OF THE INVENTION

The invention relates to implantable medical devices such as pacemakers, implantable cardioverter defibrillators (ICDs) and cardiac resynchronization therapy (CRT) devices and in particular to impedance or admittance-based techniques for use by such devices to estimate left atrial pressure (LAP) for use in detecting heart failure, pulmonary edema or related conditions.

BACKGROUND OF THE INVENTION

Heart failure is a debilitating disease in which abnormal function of the heart leads to inadequate blood flow to fulfill the needs of the tissues and organs of the body. Typically, the heart loses propulsive power because the cardiac muscle loses capacity to stretch and contract. Often, the ventricles do not adequately fill with blood between heartbeats and the valves regulating blood flow become leaky, allowing regurgitation or back-flow of blood. The impairment of arterial circulation deprives vital organs of oxygen and nutrients. Fatigue, weakness and the inability to carry out daily tasks may result. Not all heart failure patients suffer debilitating symptoms immediately. Some may live actively for years. Yet, with few exceptions, the disease is relentlessly progressive. As heart failure progresses, it tends to become increasingly difficult to manage. Even the compensatory responses it triggers in the body may themselves eventually complicate the clinical prognosis. For example, when the heart attempts to compensate for reduced cardiac output, it adds cardiac muscle causing the ventricles to grow in volume in an attempt to pump more blood with each heartbeat, i.e. to increase the stroke volume. This places a still higher demand on the heart's oxygen supply. If the oxygen supply falls short of the growing demand, as it often does, further injury to the heart may result, typically in the form of myocardial ischemia or myocardial infarction. The additional muscle mass may also stiffen the heart walls to hamper rather than assist in providing cardiac output. Often, electrical and mechanical dyssynchronies develop within the heart such that the various chambers of the heart no longer beat in a synchronized manner, degrading overall cardiac function.

A particularly severe form of heart failure is congestive heart failure (CHF) wherein the weak pumping of the heart, compromised filling or valvular dysfunction leads to build-up of fluids (i.e. congestion) in the lungs and other organs and tissues. The accumulation of fluids in the lungs to heart failure is referred to herein as cardiogenic pulmonary edema (PE). Briefly, the poor cardiac function resulting from heart failure can cause blood to back up in the lungs, thereby increasing blood pressure in the lungs, particularly pulmonary venous pressure. Alternatively, a malfunctioning mitral valve which becomes incompetent (i.e., leaky) may result in mitral valve regurgitation that can produce acute elevation in left atrial pressure during left ventricular contraction with increased propensity to developing PE. The increased pressure pushes fluid—but not blood cells—out of the blood vessels and into lung tissue and air sacs (i.e. the alveoli). This can cause severe respiratory problems and, if left untreated, can be fatal. Note that noncardiogenic forms of PE can arise due to factors besides heart failure, such as infection. More specifically, noncardiogenic PE can be caused by changes in permeability of the pulmonary capillary membrane as a result of either a direct or an indirect pathologic insult.

Many patients susceptible to CHF and cardiogenic PE, particularly the elderly, have pacemakers, ICDs, CRT devices or other implantable medical devices implanted therein, or are candidates for such devices. Accordingly, it is desirable to provide techniques for detecting and tracking CHF and cardiogenic PE using such devices. One particularly effective parameter for detecting and tracking CHF is cardiac pressure, particularly left atrial pressure (LAP), i.e. the blood pressure within the left atrium of the patient. Reliable detection of LAP would not only permit the implanted device to track CHF/PE for diagnostic purposes but to also control therapies applied to address CHF/PE such as CRT. In this regard, CRT seeks to normalize asynchronous cardiac electrical activation and the resultant asynchronous contractions by delivering synchronized pacing stimulus to the ventricles using pacemakers, ICDs or CRT devices equipped with biventricular pacing capability. The pacing stimulus is typically synchronized so as to help to improve overall cardiac function. This may have the additional beneficial effect of reducing the susceptibility to life-threatening tachyarrhythmias. CRT and related therapies are discussed in, for example, U.S. Pat. No. 6,643,546 to Mathis et al., entitled "Multi-Electrode Apparatus And Method For Treatment Of Congestive Heart Failure"; U.S. Pat. No. 6,628,988 to Kramer et al., entitled "Apparatus And Method For Reversal Of Myocardial Remodeling With Electrical Stimulation"; and U.S. Pat. No. 6,512,952 to Stahmann et al., entitled "Method And Apparatus For Maintaining Synchronized Pacing." Reliable estimates of LAP would also allow the dosing of heart failure medications (such as diuretics) to be properly titrated so as to minimize the number of episodes of acute heart failure decompensation. That is, accurate LAP monitoring can provide for the early identification of incipient HF decompensation and guide the adjustment of vasodilator and diuretic dosing. See, also, Ritzema et al., "Physician-directed patient self-management of left atrial pressure in advanced chronic heart failure," Circulation 2010; 121:1086-1095.

However, LAP is a difficult parameter to detect since it is not clinically appealing to place a blood pressure sensor directly in the left atrium due to the chronic risk of thromboembolic events, as well as risks associated with the transseptal implant procedure itself. Accordingly, various techniques have been developed for estimating LAP based on other parameters that can be more safely sensed by a pacemaker or ICD. In this regard, some particularly promising techniques have been developed that use electrical impedance signals (or related electrical signals such as admittance) to estimate LAP. For example, impedance signals can be sensed along three sensing vectors that form a triangle in which one of the vertices includes an electrode mounted on a left ventricular (LV) lead. The near-field impedance associated with the electrode mounted on the LV lead may be derived using the various "near-field" based impedance techniques described in U.S. patent application Ser. No. 12/853,130, filed concurrently herewith, of Gutfinger et al., entitled "Near Field-Based Systems and Methods for Assessing Impedance for Use by an Implantable Medical Device," which is also fully incorporated by reference herein. The sensed near-field impedance associated with an electrode mounted on the LV lead is affected by the blood volume inside the left ventricle, which is in turn reflected by the blood volume and pressure in the left atrium. Accordingly, there is a correlation between the derived near-field impedance associated with the electrode mounted on the LV lead and LAP, which can be exploited to estimate LAP and thereby also detect and/or track CHF and warn of cardiogenic PE.

For LAP estimation techniques based on impedance, admittance or related electrical parameters see: U.S. patent application No. 11/559,235, filed Nov. 13, 2006, of Gutfinger et al., entitled "System and Method for Estimating Cardiac Pressure Using Parameters Derived from Impedance Signals Detected by an Implantable Medical Device", which is incorporated by reference herein, as well as U.S. patent application Ser. Nos. 11/558,101; 11/557,851; 11/557,870; 11/557,882; and 11/558,088, each entitled "Systems and Methods to Monitor and Treat Heart Failure Conditions." See, also, U.S. patent application Ser. No. 11/558,194, by Panescu et al., entitled "Closed-Loop Adaptive Adjustment of Pacing Therapy based on Cardiogenic Impedance Signals Detected by an Implantable Medical Device". Still further, see U.S. patent application Ser. No. 12/109,304, filed Apr. 25, 2008, of Gutfinger et al., entitled "System and Method for Calibrating Cardiac Pressure Measurements Derived from Signals Detected by an Implantable Medical Device". Still further, see, U.S. patent application Ser. No. 12/712,003, of Gutfinger, filed Feb. 24, 2010, entitled "Device and Method for Adjusting Impedance Based on Posture of a Patient."

At least some of these documents describe cardiac pressure estimation techniques wherein a linear correlation between LAP and impedance (Z)—or related electrical signals such as admittance (Y) or conductance (G)—is exploited by the implanted device to estimate LAP. Briefly, the electrical signals are measured along sensing vectors passing through the heart of the patient in response to impedance-detection pulses generated by the device. Transformations are used to derive the near-field impedance measurements associated with various electrodes. Suitable conversion factors are determined via linear regression (or other suitable techniques) to relate the particular measured electrical signal parameter to LAP, so that measurements can then be used to estimate LAP. In one particular example, the conversion factors are "slope" and "baseline" values representative of the linear correlation between LAP and electrical parameter values measured in response to the impedance-detection pulses. Slope may also be referred to as "gain." Baseline may also be referred to as "offset" or bLAP (i.e. baseline LAP.) Thereafter, LAP is estimated using:

$$zLAP = Parameter*Slope + Baseline$$

wherein "Parameter" is the electrical parameter measured in response to the impedance detection pulses and zLAP represents the estimated LAP. Note that for the sake of generality, the term zLAP is used herein to refer to estimated LAP values whether based on actual impedance signals, or any of the related electrical signals such as admittance or conductance.

Although the foregoing techniques are helpful, there remains room for further improvement. One concern with using zLAP estimates is that the presence of acute mitral valve regurgitation (MR) can introduce errors into the LAP estimate. In this regard, if acute MR develops, a sudden increase in actual LAP can occur within the patient without a significant immediate change in impedance (or related parameters such as admittance) from which LAP is estimated. If MR becomes sustained (i.e. chronic), impedance values can start to change but with a lag relative to the rise in actual LAP. When chronic MR acutely resolves, there can be a sudden decrease in LAP without any immediate change in impedance. Impedance eventually changes but again with a lag relative to actual LAP. This phenomenon, which is discussed in greater detail below, can affect the capability of an implantable device to properly estimate LAP based on impedance/admittance within patients subject to acute MR.

Accordingly, it is desirable to provide techniques for estimating LAP estimates that takes into account the presence or absence of acute MR within the patient. It is to this end that the invention is primarily directed.

SUMMARY OF THE INVENTION

In accordance with an exemplary embodiment of the invention, a method is provided for use with an implantable medical device—such as a pacemaker, ICD or CRT device—for estimating cardiac pressure based on impedance (or related electrical values such as immittance, admittance or conductance or any other generally equivalent electrical values or parameters) and which takes into account the presence of acute MR within the patient in which the device is implanted. Briefly, the device detects an indication of acute MR, if occurring within the patient. The device also applies electrical fields to tissues of the patient including cardiac tissues and measures an electrical parameter influenced by the applied electrical field and affected by cardiac pressure. The electric field applied to the tissues can be, for example, a series of impedance/admittance pulses and the electrical parameter influenced by the applied field can be, e.g., an admittance, impedance or conductance. The device then estimates cardiac pressure within the patient based on the measured electrical parameter and the indication of acute MR. That is, LAP or other cardiac pressure values are estimated within the patient while accounting for the presence or absence of acute MR.

In an illustrative implementation, in addition to detecting the presence of acute MR, the device also preferably determines the severity of the condition, such as by distinguishing among trace, mild, moderate and severe forms of acute MR. In one example, acute MR and its severity is detected and assessed based on one or more of: (a) heart sounds; (b) relative changes in admittance associated with LV-sided and RV-sided electrodes; (c) relative changes in a cardiogenic impedance waveform affected by acute MR; (d) systemic blood pressure associated with an increased afterload; (e) activity and/or posture sensor signals associated with increased afterload and acute MR; (f) the presence of cardiac ischemia as detected based, e.g., on changes in ST elevation observed within an intracardiac electrogram (IEGM); and (g) the relative timing between the atrial and ventricular contractions as determined from the IEGM.

In the illustrative implementation, assuming acute MR has not been detected within the patient, the following equation is used to estimate LAP based on admittance:

$$zLAP = Admittance*Slope + Baseline$$

wherein Slope and Baseline are conversion factors representative of a linear correlation between admittance and LAP. Alternatively, exponential, polynomial or other suitable correlation functions can be employed to estimate LAP. Conversely, if acute MR has been detected within the patient, the following equation is instead used to estimate LAP based on admittance:

$$zLAP = Admittance*Slope + Baseline + Correction(MR)$$

wherein Correction(MR) is a correction term for compensating for the presence of acute MR within the patient. As with the non-MR case, exponential or polynomial functions can instead be employed to estimate LAP from admittance. Moreover, depending upon the particular implementation, the MR correction term can take into account the severity of MR. For example, a different correction term can be used for severe acute MR as opposed to mild acute MR. Still further, the correction term can take into account LV volume, if LV volume has been measured or detected within the patient.

Thus, various techniques are provided for estimating LAP and other cardiac pressure values, which takes into account the presence of possible acute MR within the patient. Various method, system and apparatus examples of these techniques are described below.

BRIEF DESCRIPTION OF THE DRAWINGS

Further features and advantages of the invention may be more readily understood by reference to the following description taken in conjunction with the accompanying drawings, in which.

DESCRIPTION OF THE PREFERRED EMBODIMENTS

The following description includes the best mode presently contemplated for practicing the invention. The description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Overview of Implantable Medical System

Figure 1:
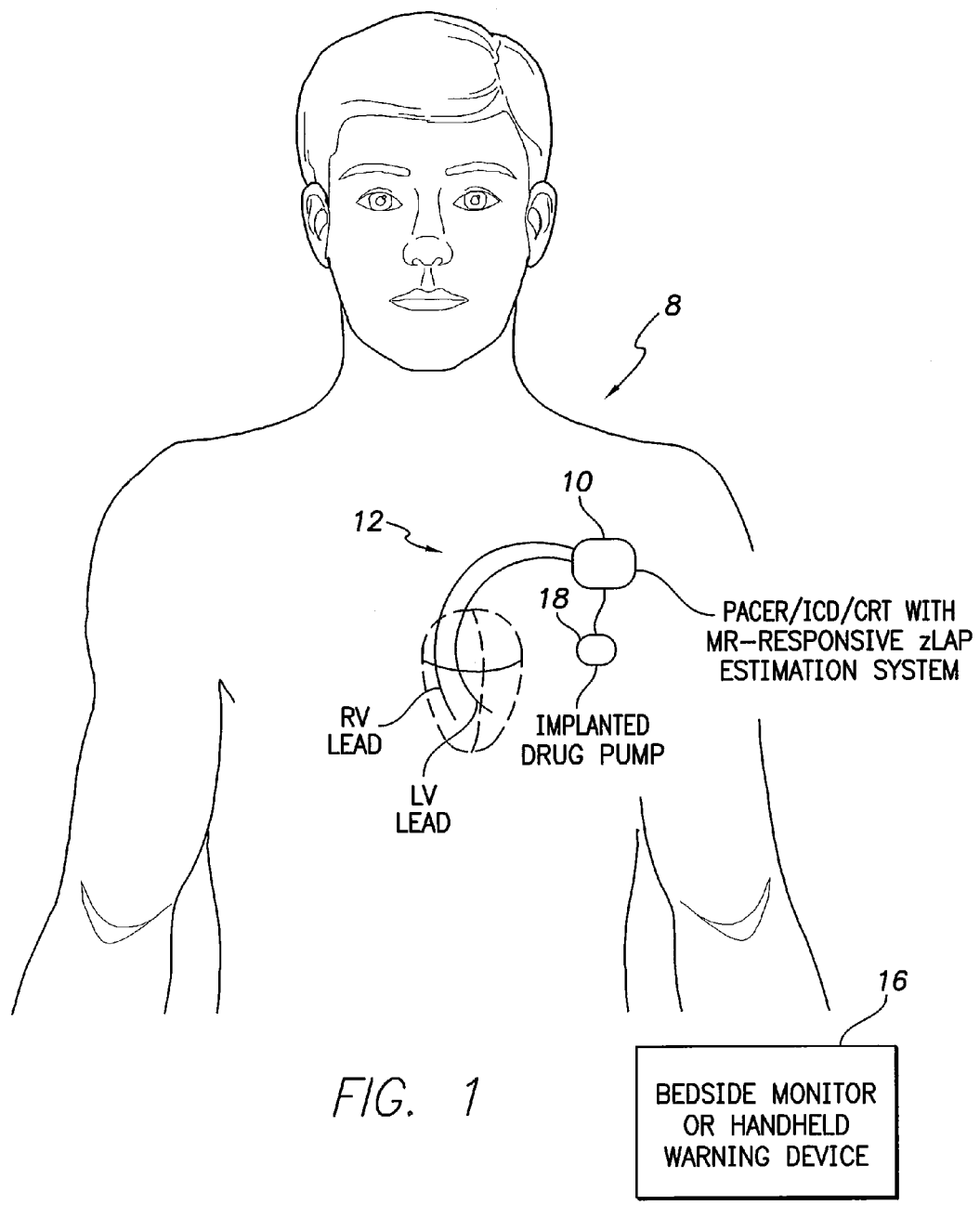
FIG. 1 is a stylized representation of an exemplary implantable medical system equipped with an MR-responsive zLAP estimation system.
Figure 6:
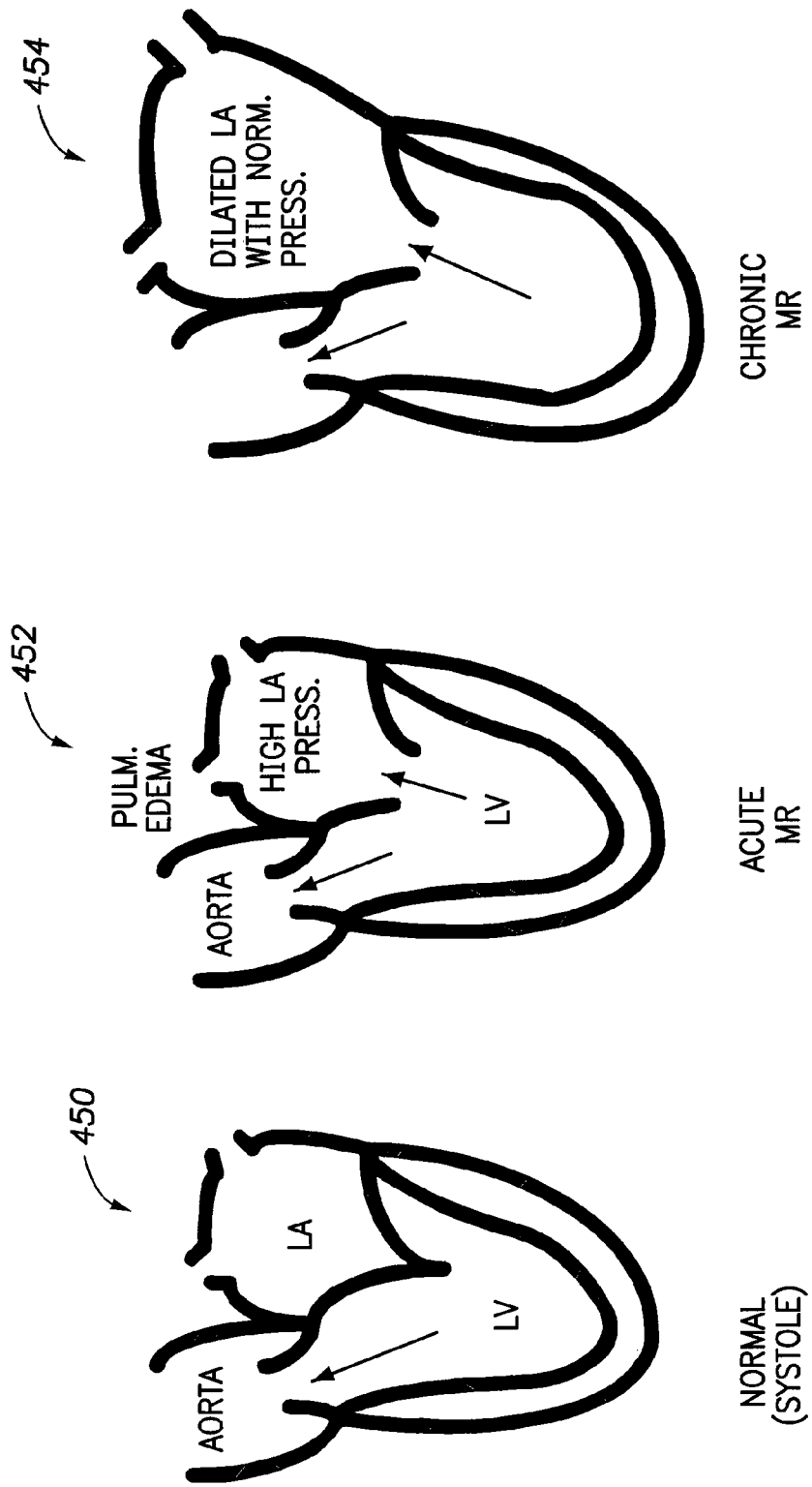
FIG. 6 is a stylized drawing illustrating the effects of acute and chronic MR on LAP, which is exploited by the method of FIG. 3.

FIG. 1 provides a stylized representation of an exemplary implantable pacing medical system 8 capable of estimating LAP based on the impedance, admittance or related signals (i.e. capable of determining zLAP values) while taking into account the presence or absence of acute MR. To this end, implantable medical system 8 includes a pacer/ICD/CRT device 10 or other cardiac stimulation device equipped to detect an indication of acute MR within the patient based on impedance, heart sounds or other parameters and, if acute MR is present, to assess its severity. The device is also equipped to deliver impedance/admittance detection pulses to the heart of the patient using electrodes mounted to a set of sensing/pacing leads 12 and further equipped to determine zLAP values from signals sensed in response to the detection pulses while taking into account acute MR, if present. That is, device 10 includes an MR-responsive zLAP estimation system. For brevity herein, the device will be referred to as a pacer/ICD but it should be understood that other devices such as standalone CRT devices may instead be employed. Note also that in FIG. 1, only two leads are shown. A more complete set of leads is illustrated in FIG. 6, which is discussed below.

Within exemplary implementations described herein, zLAP is determined based on admittance values derived from electrical signals detected in response to the impedance/admittance detection pulses. Different sets of conversion factors are stored within the pacer/ICD for use in converting the admittance values into zLAP values depending on whether the patient is presently suffering an episode of acute MR. In some examples, as will be explained, the conversion factors can further take into account the severity of the acute MR. In some implementations, the device also selectively suspends/cancels the zLAP estimation procedure based on an assessment of the reliability of the zLAP estimate made based on an analysis of various cardioelectric and cardiomechanical parameters.

See, also, the various "near field"-based impedance techniques described in U.S. patent application Ser. No. 12/853,130, filed concurrently herewith, of Guffinger et al., entitled "Near Field-Based Systems and Methods for Assessing Impedance and Admittance for Use by an Implantable Medical Device," which is fully incorporated by reference herein.

The pacer/ICD can also be equipped to track changes in zLAP so as to detect and track HF and/or cardiogenic PE. In response to HF, CRT therapy may be initiated and controlled by the implanted device. Techniques for performing CRT are discussed in the patents of Mathis et al., Kramer et al., and Stahmann et al., cited above. CRT parameters may be adaptively adjusted to improve the effectiveness of CRT using techniques set forth in the Panescu et al. patent application, "Closed-Loop Adaptive Adjustment of Pacing Therapy based on Cardiogenic Impedance Signals Detected by an Implantable Medical Device," cited above. Additionally or alternatively, the pacer/ICD can issue warning signals, if warranted. For example, if zLAP exceeds a threshold indicative of HF or is rapidly increasing toward the threshold, warning signals may be generated to warn the patient, either using an internal warning device (which can be part of the pacer/ICD) or using an external bedside monitor/handheld warning device 16. The internal warning device may be a vibrating device or a "tickle" voltage device that, in either case, provides perceptible stimulation to the patient to alert the patient so that the patient may consult a physician. In one example, once the warning is felt, the patient positions an external warning device above his or her chest. The handheld device, which might be a personal advisory module (PAM), receives short-range telemetry signals from the implanted device and provides audible or visual verification of the warning signal. The handheld warning device thereby provides confirmation of the warning to the patient, who might otherwise be uncertain as to the reason for the internally generated warning signal. For further information regarding this warning/notification technique, see U.S. patent application Ser. No. 11/043,612, of Kil et al., filed Jan. 25, 2005.

If a bedside monitor is provided, the bedside monitor provides audible or visual alarm signals to alert the patient or caregivers, as well as providing textual or graphic displays. In addition, any diagnostic information pertaining to the deteriorating cardiac condition of the patient is transferred to the bedside monitor or is stored within the pacer/ICD for subsequent transmission to an external programmer or internet network site (not shown in FIG. 1) for review by a physician or other medical professional. The physician may then prescribe therapies to address the condition. The physician may also adjust the operation of the pacer/ICD to activate, deactivate or otherwise control any therapies that are automatically applied. The bedside monitor may be directly networked with a centralized computing system, such as the HouseCall™ remote monitoring system or the Merlin.Net system of St. Jude Medical, for immediately notifying the physician of any significant increase in zLAP. Networking techniques for use with implantable medical systems are set forth, for example, in U.S. Pat. No. 6,249,705 to Snell, entitled "Distributed Network System for Use with Implantable Medical Devices."

In addition to CRT, other forms of therapy may also be controlled by the pacer/ICD in response to changes in zLAP. In this regard, if the implanted system is equipped with a drug pump 18, appropriate medications may be automatically administered upon detection of a significant increase in zLAP due to heart failure or cardiogenic PE. For example, medications may be delivered directly to the patient via the drug pump, if warranted. Alternatively, if a drug pump is not available, the patient may be provided with instructions—generated depending on the zLAP values—specifying the dosage of various heart failure medications to be taken orally. Exemplary heart failure medications include angiotensin-converting enzyme (ACE) inhibitors such as captopril, enalapril, lisinopril and quinapril, diuretics, digitalis, nitrates, beta-blockers, angiotensin receptor blockers (ARB), and other compounds. Depending upon the particular medication, alternative compounds (e.g., intravenous or subcutaneous agents) may be required for use in connection with an implantable drug pump. Routine experimentation may be employed to identify medications for treatment of heart failure or other conditions that are safe and effective for use in connection with an implantable drug pump. Dosages may be titrated based upon the severity of heart failure as determined from zLAP or other parameters.

Various techniques may be employed to confirm the detection of heart failure (or other medical conditions) made by the pacer/ICD before therapy is delivered. Exemplary heart failure detection/evaluation techniques are set forth in: U.S. Pat. No. 6,748,261, entitled "Implantable medical device for and Method of Monitoring Progression or Regression of Heart Disease by Monitoring Interchamber Conduction Delays"; U.S. Pat. No. 6,741,885, entitled "Implantable Cardiac Device for Managing the Progression of Heart Disease and Method"; U.S. Pat. No. 6,643,548, entitled "Implantable Medical Device for Monitoring Heart Sounds to Detect Progression and Regression of Heart Disease and Method Thereof"; U.S. Pat. No. 6,572,557, entitled "System and Method for Monitoring Progression of Cardiac Disease State using Physiologic Sensors"; and U.S. Pat. No. 6,480,733, entitled "Method for Monitoring Heart Failure," each assigned to Pacesetter, Inc.

Figure 2:
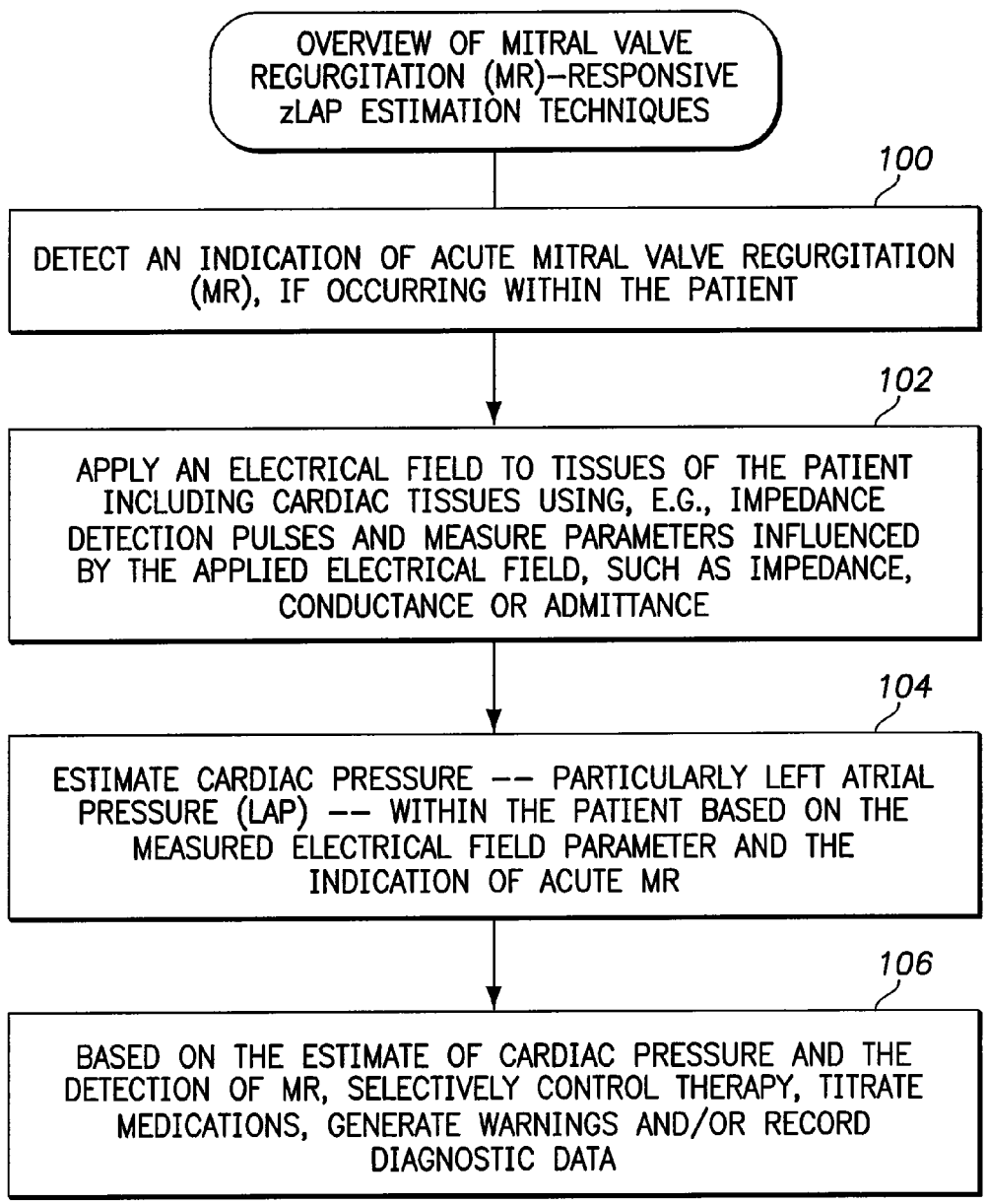
FIG. 2 provides an overview of techniques for estimating zLAP while accounting for acute MR within the patient that may be performed by the system of FIG. 1.

FIG. 2 broadly summarizes the MR-responsive LAP estimation techniques performed by the pacer/ICD of FIG. 1 or other suitably-equipped implantable devices. At step 100, the device detects an indication of acute MR, if occurring within the patient. Techniques for detecting acute MR will be described below with reference to FIG. 3. At step 102, the device applies an electrical field to tissues of the patient including cardiac tissues (such as by applying a series of impedance/admittance detection pulses along a vector through the heart) and measures at least one electrical parameter influenced by the applied electrical field, such as admittance, impedance or conductance. At step 104, the device estimates cardiac pressure—particularly LAP—within the patient based on the measured electrical field parameter and the indication of acute MR. That is, at step 104, the device determines zLAP while accounting for the presence or absence of acute MR. Various exemplary zLAP determination techniques are described in the above-cited applications, such as U.S. patent application Ser. No. 11/559,235, incorporated by reference herein. An exemplary admittance-based zLAP technique that specifically takes into account the presence or absence of acute MR is discussed below in connection with FIG. 7. At step 106, based on the estimate of cardiac pressure (e.g. zLAP) and the detection of a possible acute MR, the device selectively controls therapy, titrates medications, generates warnings and/or records diagnostic data. For example, the warnings can indicate the presence of acute MR and/or a high LAP value, or both.

Hence, FIGS. 1 and 2 provide an overview of an implantable medical system/method for estimating LAP while accounting for acute MR and for delivering appropriate warning/notification signals and therapy in circumstances where such actions are warranted. Embodiments may be implemented that do not necessarily perform all of these functions. For example, embodiments may be implemented that estimate LAP but do not automatically initiate or adjust HF therapy. Moreover, systems provided in accordance with the invention need not include all of the components shown in FIG. 1. In many cases, for example, the system will include only a pacer/ICD/CRT and its leads. Implantable warning devices and drug pumps are not necessarily implanted. Some implementations may employ an external monitor for displaying warning signals without any internal warning device. These are just a few exemplary embodiments. No attempt is made herein to describe all possible combinations of components that may be provided in accordance with the general principles of the invention. In addition, note that the particular locations of the implanted components shown in FIG. 1 are merely illustrative and may not necessarily correspond to actual implant locations. Although internal signal transmission lines provided are illustrated in FIG. 1 for interconnecting various implanted components, wireless signal transmission may alternatively be employed, where appropriate.

Exemplary MR-responsive zLAP Estimation Techniques

Figure 3:
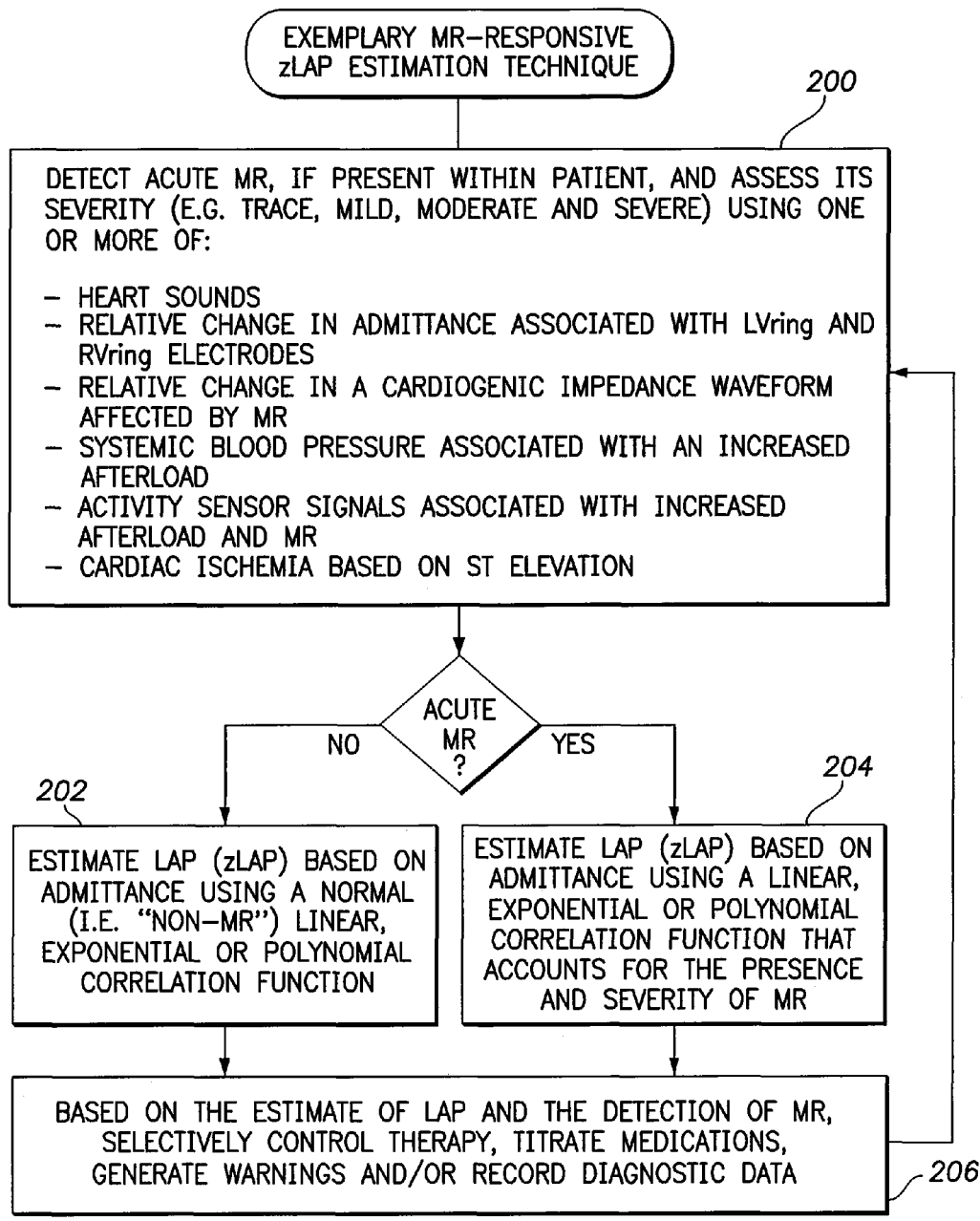
FIG. 3 illustrates an exemplary method performed in accordance with the general technique of FIG. 2, wherein the zLAP estimation procedure exploits admittance and takes into account the presence or absence of acute MR.

Referring next to FIG. 3, an illustrative zLAP estimation technique will be described that takes into account the presence or absence of acute MR within the patient, as well as its severity. Beginning at step 200, the pacer/ICD detects acute MR, if present within patient, and assesses its severity (e.g. trace, mild, moderate and severe) using one or more of: (a) heart sounds; (b) a relative change in admittance associated with LV-sided and RV-sided electrodes; (c) a relative change in a cardiogenic impedance waveform affected by MR; (d) changes in systemic blood pressure associated with an increased afterload; (e) activity sensor signals associated with increased afterload and MR; (f) the presence of cardiac ischemia as detected based, e.g., on increase in ST elevation; and (g) the relative timing of the atrial and ventricular contractions. Depending upon the particular MR detection technique, one or more thresholds may be specified for detecting the onset of an episode of acute MR and for assessing its severity (e.g. for classifying the MR as trace, mild, moderate and severe.)

Insofar as heart sounds are concerned, such sounds generally correspond to the closure of valves within the heart and may be detected using acoustic sensors or accelerometers. Briefly, a first (S1) heart sound is associated with closure of the mitral valve. A second (S2) heart sound is associated with closure of the aortic and pulmonic valves. See, for example, U.S. Pat. No. 7,139,609, of Min et al., entitled "System and Method for Monitoring Cardiac Function via Cardiac Sounds using an Implantable Cardiac Stimulation Device." Mitral regurgitation produces certain predictable changes in the heart sounds produced by valve closure. These changes become more pronounced as the severity of the regurgitation increases. See, for example, U.S. patent application 2006/0173505 of Salo et al. "Controlled Delivery of Electrical Pacing Therapy for Treating Mitral Regurgitation."

Changes in admittance (or related parameters such as impedance and conductance) associated with electrodes mounted on a LV-sided pacing lead (e.g., LVring) and a RV-sided pacing lead (e.g., RVring) can be used to detect acute MR, and assess its severity, by comparing over-time the relative trends in the near-field admittances associated with the LV-sided and RV-sided electrodes. Specifically, using the near-field model transformation described in the above-referenced co-pending patent applications, the near-field impedances associated with the LV-sided and RV-sided electrodes are derived, and subsequently converted into corresponding admittance measurements. The near-field admittance associated with the LV-sided electrode reflects the LV volume, while the near-field admittance associated with the RV-sided electrode reflects RV volume. When acute MR develops, there is an immediate increase in LAP and an associated increase in RV volume in a patient with a history of heart failure. However, the LV volume will not change immediately to acute MR and will remain relatively fixed or may even decrease initially.

The sudden increase in RV volume produces a corresponding sudden increase in the near-field admittance associated with the RV-sided electrode, while there is no corresponding increase in the near-field admittance associated with the LV-sided electrode when the LV volume remains fixed. This sudden increase in the near-field admittance associated with the RV-sided electrode in the absence of a corresponding increase in the near-field admittance associated with the LV-sided electrode is utilized as an indication for detecting acute MR. A patient specific threshold can be determined for detecting the presence or absence of acute MR based on a review of in-clinic real-time impedance measurements obtained during a physiologic stress study, such as a bicycle exercise test or a bilateral isometric hand grip exercise, that lead to producing a short episode of acute MR. The in-clinic evaluation may be supplemented with a simultaneous echocardiogram study to further verify the presence or absence of acute MR during the stress study. Patients that do not demonstrate the required changes in the impedance signals or echocardiogram data within the in-clinic evaluation session may be labeled as not being suitable candidates for the MR-detection algorithm being proposed here, but may be suitable for an alternative approach for detecting acute MR described herein.

The severity of the detected acute-MR may be determined based on the degree to which the patient specific threshold is exceeded. This can be further verified within the in-clinic evaluation process and correlated with findings on an echocardiogram.

Changes in cardiogenic impedance waveforms (or related cardiogenic waveforms such as admittance and conductance) can be used to detect acute MR and assess its severity by relying on an intra-cardiac electrode that is placed within the left atrium or in a vicinity of the left atrium (e.g., coronary sinus). The near-field impedance waveform for the electrode positioned within the left atrium is utilized and the corresponding admittance waveform is derived from its reciprocal. The admittance waveform for a left atrial electrode reflects left atrial volume. In the presence of acute MR, the V-wave corresponding to venous filling within the left atrium would tend to increase relative to the A-wave corresponding to the atrial contraction. During acute MR, the V-wave will increase significantly as a result of left ventricular contraction of blood back into the left atrium. A sudden increase in the size of the V-wave relative to the size of an A-wave in the admittance waveform for the left atrial electrode would be indicative of an acute episode of MR. This can similarly be verified and studied for an optimal threshold with corresponding boundaries for determining severity within an in-clinic evaluation using a stress test in combination with simultaneous echocardiogram imaging.

Changes in systemic blood pressure (as detected using a suitable pressure sensor or sensing technique) associated with an increased afterload can be used to detect acute MR, since acute MR is more common when afterload is significantly increased. More specifically, systemic blood pressure can be used to detect acute MR and assess its severity by declaring the presence or absence of acute MR whenever the mean systemic blood pressure (i.e., afterload) exceeds a pre-defined threshold. Patients that tend to develop episodes of acute MR tend to be extremely sensitive to an increase in afterload. Patients are studied and examined in advance within an in-clinic setting using a blood pressure cuff and an echocardiogram in order to determine a reliable threshold for the mean blood pressure for which acute MR develops. Within an "in-clinic" setting, afterload can be acutely increased with an isometric bilateral handgrip exercise. The severity of MR tends to increase with higher afterload such that pre-defined patient-specific boundaries for severity can be determined within the in-clinic evaluation stress test.

Changes in activity (as detected using a suitable activity sensor) associated with an increased afterload can be used to detect acute MR and assess its severity by determining the presence or absence of MR in the setting of increased activity sensed with an accelerometer that is part of the a cardiac rhythm management device. Not all patients will develop acute MR in response to increasing activity. However, the group of patients that are sensitive for developing acute MR during periods of elevated activity are determined in advance during an in-clinic evaluation session that includes a simultaneous evaluation with an echocardiogram.

Changes in ST elevation indicative of cardiac ischemia (as detected via the IEGM) can be used to detect acute MR and assess its severity in patients with ischemic MR. Patients with a history of ischemic MR tend to develop episodes of acute MR whenever blood flow to the papillary muscles is compromised. Patients with ischemic MR will tend to develop ischemia during periods of increased exercise and increased workload for the heart, which will lead to an acute episode of MR. Patients should be exercised within an in-clinic environment to demonstrate the presence of exercise induced ischemia with a corresponding episode of acute MR. This typically requires using both surface electrograms and an echocardiogram during the evaluation process. A patient specific threshold if applicable is then determined, along with boundaries for severity based on the degree of ST segment change.

Note that ST elevation can be measured within an IEGM signal detected by the device. ST elevation represents the elevation of the portion of the IEGM signal between the end of a QRS-complex and the start of the subsequent T-wave. The elevation can be measured relative to an IEGM baseline voltage. For ST elevation measurement techniques, see, e.g., U.S. patent application Ser. No. 12/016,166 of Boileau et al., filed Jan. 17, 2008, entitled "Systems and Methods for Distinguishing Cardiac Ischemia from Systemic Influences on IEGM Morphology using an Implantable Medical Device." Techniques of detecting ischemia based on the ST segment are described, for example, in U.S. patent application Ser. No. 11/757,796, of Boileau et al., entitled "System and Method for Adaptively Adjusting Cardiac Ischemia Detection Thresholds and other Detection Thresholds used by an Implantable Medical Device."

See, also, the various acute MR detection techniques discussed in U.S. Pat. No. 7,483,743 of Mann et al., entitled "System for Detecting, Diagnosing, and Treating Cardiovascular Disease" and in U.S. Pat. No. 7,717,854, also of Mann et al., entitled "Method for Detecting, Diagnosing, and Treating Cardiovascular Disease."

The presence of an acute MR episode may also be determined by trending IEGMs derived from an atrial and a ventricular lead. Patients that have a pre-mature ventricular contraction (PVC) will tend to have a very short atrio-ventricular (AV) interval and the left ventricle will contract sometimes while the mitral valve is still open and blood is emptying from the left atrium. This will produce an acute episode of MR with the production of a large V-wave. A suitable threshold specifying the AV interval that is deemed to be too short may be defined for each patient specifically by conducting an in-clinic evaluation in a patient with a biventricular pacemaker and a programmable AV interval with simultaneous review of the echocardiogram image data.

Preferably, a combination of various acute MR detection techniques are employed to detect acute MR and assess its severity so as to improve the robustness and specificity of the MR detection algorithm. In this regard, the various indicators of MR can be parameterized and combined into a patient-specific index for comparison against one or more thresholds indicative of the onset of acute MR and its severity. As can be appreciated, some of the MR detection factors (such as heart sounds) are more reliable indictors of acute MR than others and hence various weights can be applied to the different factors. Such weights can be determined in advance and programmed into the device and may be specified by, or adjusted by, the clinician. Otherwise routine experiments can be used to determine appropriate values for use as the weights and thresholds based on clinical studies from populations of patients.

Once acute MR is detected, a timer may be started to determine the duration of the acute MR episode. If the duration exceeds a particular threshold, the episode of acute MR may be declared to become a chronic episode of MR. The determination of zLAP from admittance may be further adjusted with other parameters corresponding to a chronic episode of MR.

Figure 7:
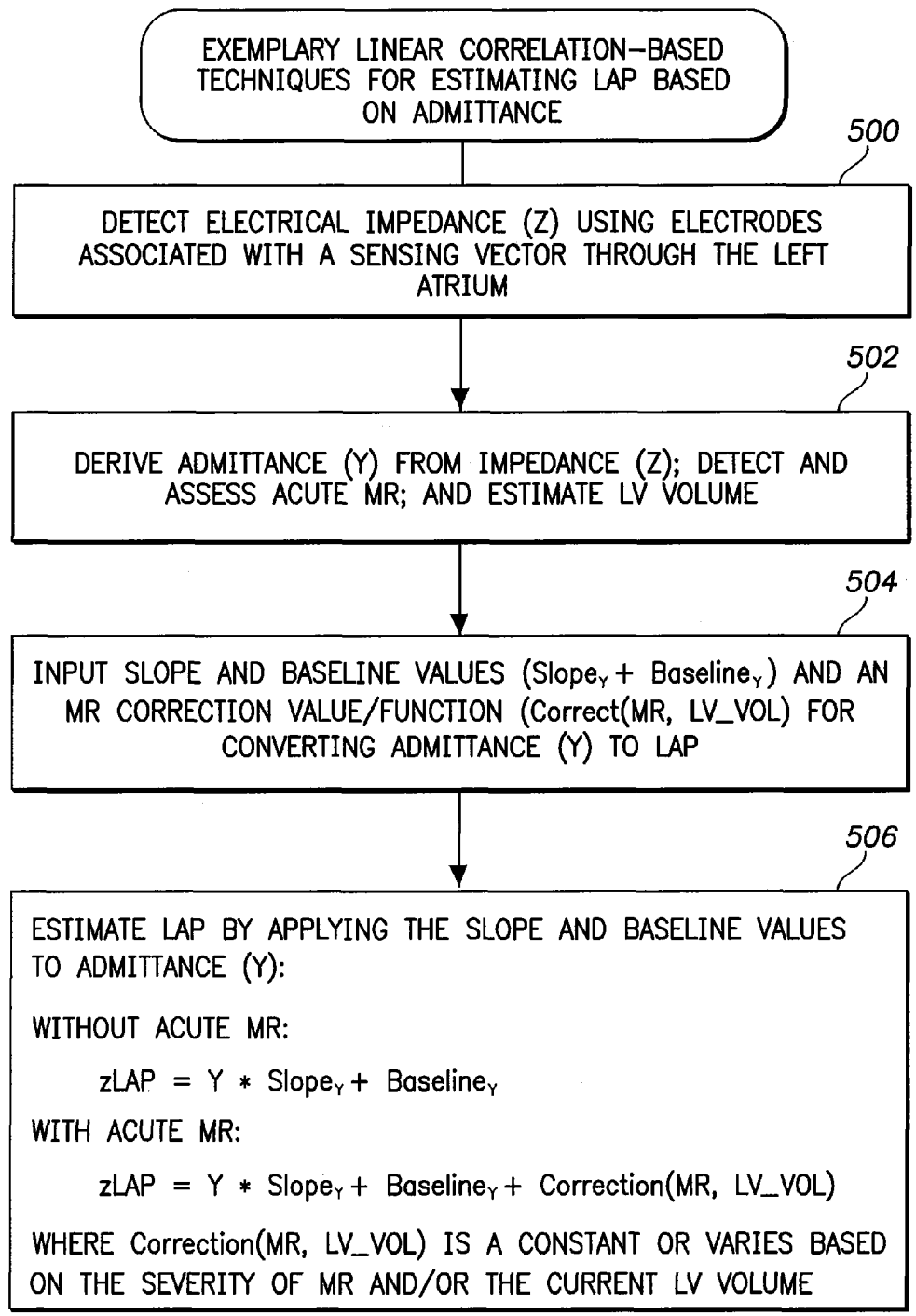
FIG. 7 summarizes an exemplary procedure for use with the technique of FIG. 3 for calculating zLAP based on admittance values derived from impedance detection pulses wherein the estimation procedure takes into account the severity of acute MR, if present within the patient.

Following step 200, if acute MR is not indicated then, at step 202, the device estimates LAP (i.e. calculates zLAP) based on admittance (or related electrical parameters) using a normal (i.e. "non-MR") correlation function. Conversely, if acute MR is indicated then, at step 204, the device estimates LAP using correlation function that accounts for the presence and severity of MR. Depending upon the implementation, the correlation function can be linear, exponential, polynomial, or other suitable function. A linear correlation function is illustrated in FIG. 7. Depending upon the implementation, the correlation functions used at steps 202 and 204 can be linear, exponential, polynomial, or other suitable function. A linear function example is discussed in FIG. 7.

At step 206, based on the estimate of LAP and the detection of MR, the device selectively controls therapy, titrates medications, generates warnings and/or records diagnostic data, as already discussed.

Note that, in implementations where therapy is automatically delivered in response to an elevated LAP due to heart failure or cardiogenic PE, the pacer/ICD might be equipped to employ at least one other detection technique to corroborate the detection of the medical condition before therapy is delivered. Techniques for detecting or tracking heart failure are set forth the following patents and patent applications: U.S. Pat. No. 6,328,699 to Eigler et al., entitled "Permanently Implantable System and Method for Detecting, Diagnosing and Treating Congestive Heart Failure"; U.S. Pat. No. 6,970,742 to Mann et al., entitle "Method for Detecting, Diagnosing, and Treating Cardiovascular Disease"; U.S. Pat. No. 7,115,095 to Eigler et al., entitled "Systems and Methods for Detecting, Diagnosing and Treating Congestive Heart Failure"; U.S. patent application Ser. No. 11/100,008, of Kil et al., entitled "System and Method for Detecting Heart Failure and Pulmonary Edema based on Ventricular End-Diastolic Pressure using an Implantable Medical Device," filed Apr. 5, 2005; U.S. patent application Ser. No. 11/014,276, of Min et al., entitled "System and Method for Predicting Heart Failure based on Ventricular End-Diastolic Volume/Pressure using an Implantable Medical Device," filed Dec. 15, 2004; U.S. patent application Ser. No. 10/810,437, of Bornzin et al., entitled "System and Method for Evaluating Heart Failure Based on Ventricular End-Diastolic Volume Using an Implantable Medical Device," filed Mar. 26, 2004 and U.S. patent application Ser. No. 10/346,809, of Min et al., entitled "System and Method for Monitoring Cardiac Function via Cardiac Sounds Using an Implantable Cardiac Stimulation Device," filed Jan. 17, 2003. See also: U.S. Pat. No. 6,572,557, to Thou et al.; U.S. Pat. No. 6,645,153, to Kroll et al., entitled "System and Method for Evaluating Risk of Mortality Due To Congestive Heart Failure Using Physiologic Sensors," and U.S. Pat. No. 6,438,408 to Mulligan et al., entitled "Implantable Medical Device for Monitoring Congestive Heart Failure."

Figure 4:
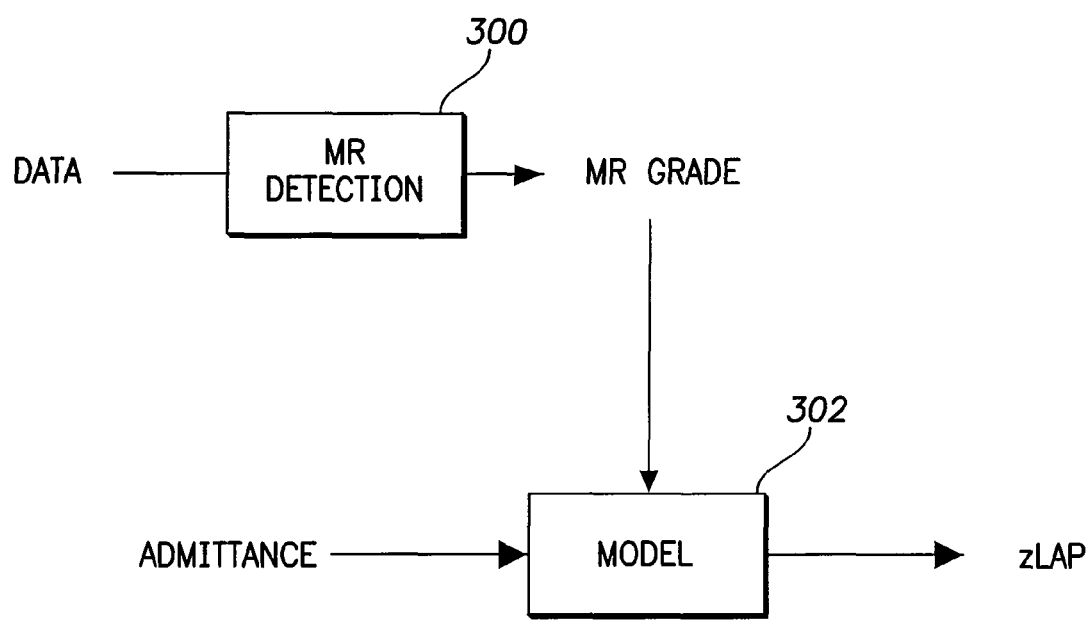
FIG. 4 is a system block diagram broadly illustrating the procedure of FIG. 3.

FIG. 4 is a system diagram broadly summarizing the technique of FIG. 3. Heart sounds, cardiogenic waveforms or other MR-responsive data is processed by an MR detection system/procedure 300 to detect MR and assess its severity (i.e. its grade). This information, along with admittance data, is input to a system/procedure/model 302 that generates an estimate of LAP using linear correlation or other suitable mapping techniques. That is, two separate "modules" are proposed for deriving zLAP based on admittance measurements. The first module is a MR detection system/process/algorithm that determines the presence or absence of acute MR and/or the grade of the acute MR. The second module derives zLAP using a linear, exponential, polynomial or other functions based on the measured admittance and the amount of MR detected. Multiple embodiments for constructing each of these modules are available. The model relating admittance to zLAP contains at least an additional correction term that is applied to the zLAP estimate to account for the presence or absence of acute MR. The correction term is preferably applied whenever acute MR is present. Depending upon the implementation, the correction term may be a simple constant, but may instead be a dynamically adjusted value based on the degree of MR and/or LV volume.

Figure 5:
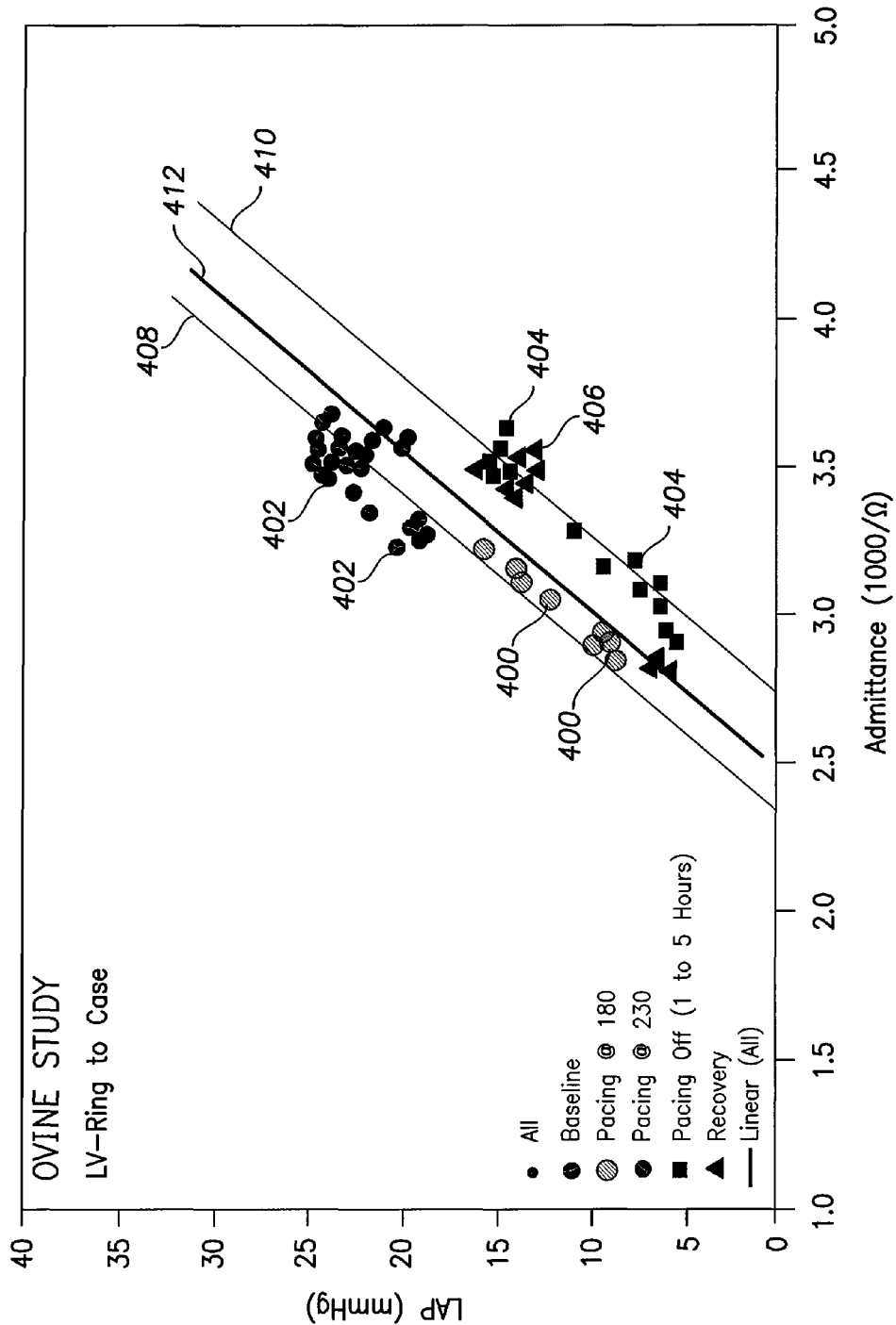
FIG. 5 is a graph illustrating the affect of acute MR on the correlation between admittance and LAP, which is exploited by the method of FIG. 3.

FIG. 5 is a graph illustrating the affect of acute MR on the correlation between admittance and LAP, which is exploited by the model of FIG. 4. More specifically, the graph illustrates the results of an ovine test wherein acute MR was induced in test subjects through rapid pacing and actual LAP was measured (rather than zLAP). A first set of data points 400 were obtained while the test subjects were paced at 180 beats per minute (bpm) to induce acute MR. In this regard, at the initiation of rapid ventricular pacing, acute cannon A-waves develop, which are representative of simultaneous atrial and ventricular contractions with attended MR. Note that both LAP and admittance rise, but admittance lags behind LAP. A second set of data points 402 were obtained while the test subjects were paced at 230 bpm to further exacerbate the MR and elevate LAP.

A third set of data points 404 were obtained during a period of one to five hours after pacing was stopped. A fourth set of data points 406 show subsequent recovery (i.e. data collected more than five hours after termination of rapid pacing.) As can be seen, when rapid ventricular pacing is stopped, LAP acutely decreases by about 10 mmHg; however, admittance does not acutely track LAP and instead decreases over a longer time duration. As such, there is a form of hysteresis triggered by the presence or absence of acute MR (as induced in this study by rapid pacing.)

This hysteresis behavior has also been observed in the clinical setting in a patient with functional MR that produced acute rises in LAP that were not associated with acute rises in admittance. It is believed that MR acutely develops when there is a sudden increase in afterload and/or dysfunction of the papillary muscle as a consequence of ischemia. If admittance derived from the LV ring electrode reflects LV volume, then the lack of change in admittance may indicate that during acute MR LV volume stays relatively fixed, while LAP acutely rises.

FIG. 6 illustrates this MR "paradox." In a normal, healthy heart 450, blood is pumped from the LV into the aorta, with the mitral valve properly closed. During acute MR 452, the mitral valve can remain open allowing at least some blood to be pumped back into the LA, resulting in high LAP. However, during chronic MR 454, the LA can become distended such that the backflow of blood from LV to LA does not result in an elevated LAP. Indeed, LAP can be normal during chronic MR.

Returning to FIG. 5, a first linear fit line 408 is shown extending through the data obtained during rapid pacing where acute MR was produced. (Note that line 404 is merely an approximation of the best linear fit to the data and does not necessarily represent the actual best fit with complete precision.) A second linear fit line 410 is shown extending through data obtained following the completion of rapid pacing during a period of time when acute MR was no longer present. (As with line 408, line 410 is merely an approximation of the best linear fit to the data.) Although the slopes of linear fit lines 408 and 410 are equal in this example, the respective baseline values (where LAP is 0 mmHg) differ significantly, indicating that different correction factor should be applied during acute MR as opposed to during periods of time when acute MR is absent. Finally, note that a linear fit line 412 is also shown, which represents the best fit to all the data. In this particular example, line 412 corresponds to zLAP=18.3*admittance−45.1 with an $R^2$ of 0.63. Although zLAP values generated using this overall "best fit" might be satisfactory for some purposes, such estimates would not be as accurate as desired and not as accurate as can be achieved when taking into account the presence or absence of acute MR. Hence, the various MR-responsive techniques described herein are preferred to improve LAP estimation accuracy.

Exemplary Admittance-based zLAP Estimation Technique

Turning now to FIG. 5, for the sake of completeness, a technique for calculating zLAP in response to admittance values derived from signals detected based on impedance detection pulses will be described in detail. This particular technique employs linear correlation using admittance values but, as noted, other techniques can be used as well to calculate zLAP. At step 500, the pacer/ICD detects electrical impedance (Z) along a sensing vector where impedance is affected by cardiac pressure, particularly LAP. For example, the cardiogenic impedance signal may be sensed between an LV tip electrode and an RA tip electrode such that the sensing vector passes through the LA. However, impedance signals sensed between other electrode pairs, such as the LV lead and the device may alternatively be utilized to indirectly estimate LAP under the presumption that, if these electrode pairs span the region containing the blood within pulmonary veins, then a resulting estimate of pulmonary venous pressure may be used as an estimate for LAP.

In the alternative, "near field"-based impedance techniques can be exploited, as described in the co-pending applications cited above and incorporated by reference herein. In order to apply the "near-field" based impedance techniques it is necessary to acquire impedance signals across at least three vectors that form a triangle. Furthermore, at least one of the vertices of the impedance triangle must include an electrode such as an LV-RING electrode or a Left Atrial (LA)-RING electrode or other electrode that has a close association with either the LV or LA blood volume. The near-field impedance signal associated with the LV-RING or LA-RING electrode can subsequently be used to derived zLAP estimates.

Continuing with a "far field"-based technique, impedance signals are obtained by transmitting a current between a pair of electrodes, and subsequently measuring the voltage between the same or another pair of electrodes. The impedance is calculated as the ratio of the measured voltage to the transmitted current. Preferably, a tri-phasic impedance pulse waveform is employed to sense the impedance signal. The tri-phasic waveform is a frequency-rich, low energy waveform that provides a net-zero charge and a net-zero voltage. An exemplary tri-phasic pulse waveform is described in detail in the related patent applications, cited above. Depending upon the particular sensing vector, it may be appropriate to filter the impedance signal to eliminate or reduce any noncardiogenic components, such as any components arising due to respiration or changes in body position of posture. Bandpass filtering is typically sufficient to filter out respiratory components.

Although the examples described herein are primarily directed to estimating LAP, other cardiac pressure values may alternatively be estimated, such as left ventricular pressure (LVP), by using impedance signals detected using appropriate sensing vectors (e.g., LV-tip electrode to RV-ring electrode or RV-Shock coil). Indeed, multiple impedance signals may be sensed using different sensing vectors passing through different chambers of the heart so as to permit the pacer/ICD to estimate cardiac pressure within different chambers of the heart, assuming appropriate conversion values have been determined and calibrated. To this end, the implanted system may be equipped, e.g., with multiple electrodes per lead or with multiple leads per chamber. Unipolar or bipolar sensing systems may be employed.

Depending upon the implementation, particular components of an initial raw impedance signal ($Z_0$) detected by the pacer/ICD are exploited, such as the high-frequency cardiogenic impedance signal ($Z_C$) representative of the beating of the heart of the patient, the low-frequency respiratory impedance signal ($Z_R$) representative of the respiration of the patient, or the ultra-low frequency circadian impedance signal representative of daily variations in the raw impedance signal ($Z_0$) or the low-frequency respiratory impedance signal ($Z_R$). Note that current state-of-the art pacer/ICDs do not typically include a detection circuit specifically for detecting circadian impedance variations. There is a cardiogenic detection circuit that extracts the cardiogenic component ($Z_C$) of the impedance signal (also referred to as cardiogenic impedance (CI)) from the raw impedance signal ($Z_0$) by substantially filtering out noncardiogenic components. There is a low frequency detection circuit that extracts the respiratory component ($Z_R$) of the impedance signal (also referred to as respiratory impedance (RI)) by substantially filtering out non-respiratory components. Circadian variations may be detected by storing the raw impedance values over a 24-hour period then processing the recorded raw values to extract circadian variations. In the predecessor applications cited above, the term "low-frequency raw impedance signal" was used to refer to the respiratory impedance signal ($Z_R$). Techniques for detecting or extracting the various components of the initial raw impedance signal are discussed in the cited applications.

At step 502, the pacer/ICD derives electrical admittance (Y) from the detected electrical impedance signals. Also, at this step, the device detects and assesses acute MR (using techniques already described) and, in some implementations, also detects or measures a parameter representative of LV volume, such as LV end systolic volume (LV ESV) or LV end diastolic volume (LV EDV). Techniques for detecting LV volumes are discussed, for example, in U.S. patent application Ser. No. 11/779,350, filed Jul. 18, 2007, entitled "System and Method for Estimating Cardiac Pressure based on Cardiac Electrical Conduction Delays using an Implantable Medical Device,". See, also, U.S. Pat. No. 4,674,518 to Salo, entitled "Method and Apparatus for Measuring Ventricular Volume."

At step 504, the pacer/ICD inputs predetermined conversion factors from memory for converting admittance to LAP (or to other cardiac pressure values). The conversion factors may be, e.g., predetermined slope and baseline values obtained during a calibration procedure employing linear regression. Different conversion factors are typically required depending upon the particular parameters derived from the electrical impedance signal. That is, different slope and baseline values are used for an admittance-based estimation than for a conductance-based estimation. LAP values estimated using different techniques might be averaged together.

At step 506, the pacer/ICD then estimates LAP or other cardiac pressure values within the patient by applying the conversion factors retrieved from memory (at step 504) to the parameter(s) derived from the electrical impedance signal (at step 502). When using slope and baseline conversion factors, LAP may be generally estimated without acute MR by using:

$$zLAP = Y * Slope_Y + Baseline_Y$$

and with acute MR by using:

$$zLAP = Y * Slope_Y + Baseline_Y + Correction(MR, LV\_VOL)$$

where Correction(MR, LV_VOL) is a constant or a value that varies based on the severity of MR and/or the current LV volume.

The formulae assume a linear relationship between cardiac pressure and the derived parameters, which is an appropriate presumption based on the particular parameters discussed herein, at least insofar as estimating LAP is concerned. Routine experimentation may be performed to determine whether a linear relationship is also suitable for use in estimating other particular cardiac pressure values, such as LVP, or is also suitable for use with other parameters that might be derived from the electrical impedance signal besides those specifically mentioned herein. Moreover, it should be understood that linear models need not necessarily be used, i.e. more sophisticated correlation models may instead by employed. Linear models are preferred in view of their simplicity. Moreover, it should be understood that the idea of adding a correction factor or other offset to account for MR is just one example of an MR-based adjustment technique. In general, the technique can exploit any of a wide variety of mathematical conversions or manipulations, based on the transformation of impedance into zLAP in presence of MR, as determined in the clinic during an acute MR creation maneuver, or as learned by the algorithms of the system.

Steps 500-506 may be repeated in a loop so as to update the estimated LAP. Depending upon the particular parameter used to estimate LAP, the estimates may be performed substantially in real-time so as to permit the pacer/ICD to continuously, or at least very frequently, calculate new LAP values. That is, in some implementations, a real-time LAP(t) function may be estimated so as to allow the pacer/ICD to track beat-to-beat changes in LAP. In particular, estimates of LAP based on admittance may potentially be performed substantially in real-time, assuming the pacer/ICD is appropriately configured. This allows the pacer/ICD to respond promptly to changes within the heart of the patient.

Note that the cardiac pressure value estimated using the techniques described herein is an effective intracardiac pressure ($P_{eff}$) not an absolute pressure. It represents the absolute intracardiac pressure less intrathoracic pressure:

$$P_{eff} = P_{intracardiac} - P_{intrathoracic}$$

That is, the effective pressure is a type of gauge pressure. Unless otherwise noted, all estimated cardiac pressure values discussed herein, particularly estimated LAP, are effective pressure values. In some examples described herein, the term "effective LAP" may be used as a reminder that effective pressures are used. In any case, effective pressure values are typically more useful from a clinical perspective than absolute pressure values.

Although primarily described with respected to examples having a pacer/ICD, other implantable medical devices may be equipped to exploit the techniques described herein. For the sake of completeness, an exemplary pacer/ICD will now be described, which includes components for performing or controlling the various functions and steps already described.

Exemplary Pacer/ICD

Figure 8:
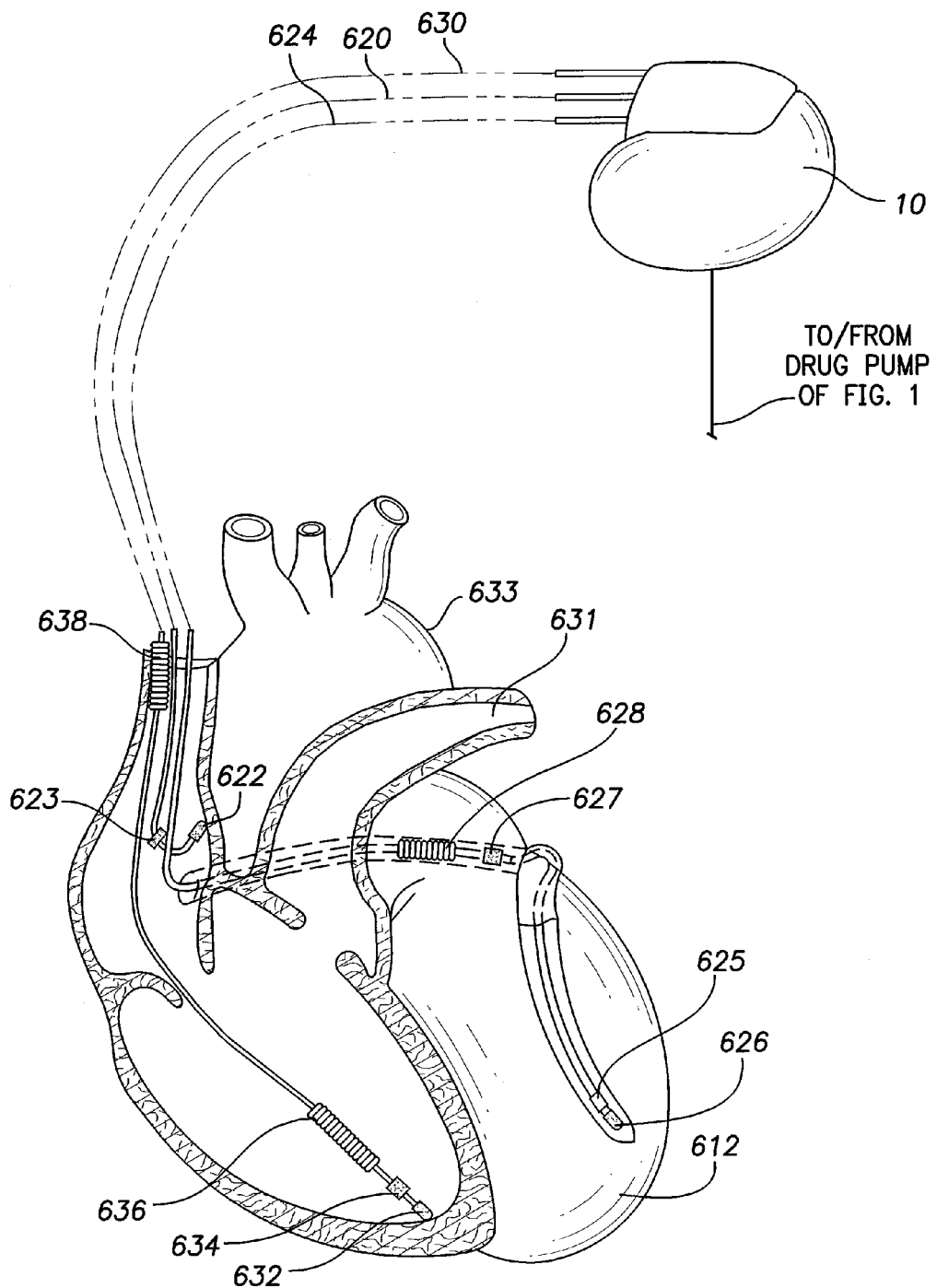
FIG. 8 is a simplified, partly cutaway view, illustrating the pacer/ICD of FIG. 1 along with a set of leads implanted in the heart of the patient.
Figure 9:
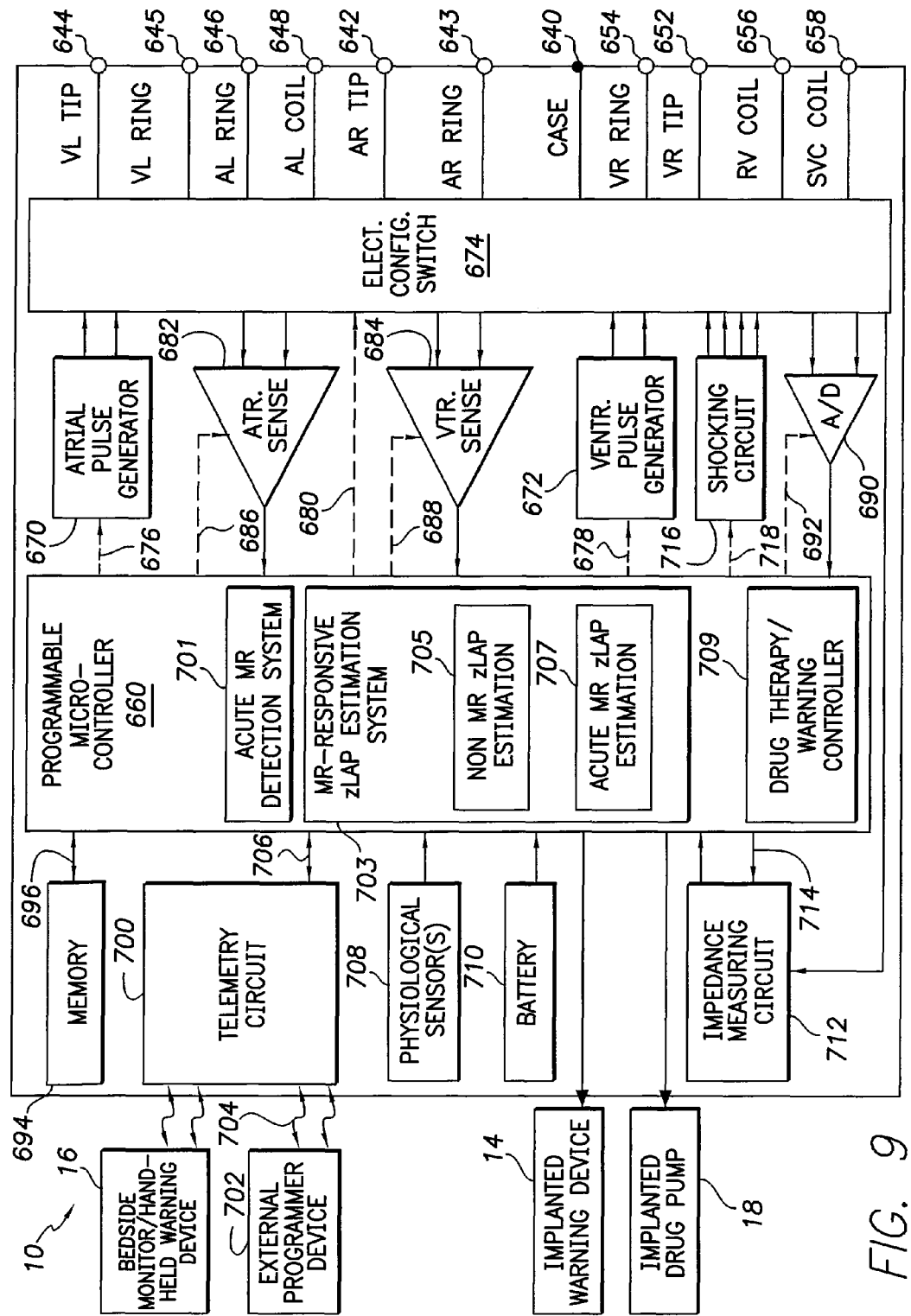
FIG. 9 is a functional block diagram of the pacer/ICD of FIG. 8, illustrating basic circuit elements that provide cardioversion, defibrillation and/or pacing stimulation in the heart and particularly illustrating components for estimating zLAP that account for a possible acute MR within the patient.

With reference to FIGS. 8 and 9, a description of an exemplary pacer/ICD will now be provided. FIG. 8 provides a simplified block diagram of the pacer/ICD, which is a dual-chamber stimulation device capable of treating both fast and slow arrhythmias with stimulation therapy, including cardioversion, defibrillation, and pacing stimulation, and also capable of estimating LAP or other forms of cardiac pressure using impedance/admittance signals. To provide other atrial chamber pacing stimulation and sensing, pacer/ICD 10 is shown in electrical communication with a heart 612 by way of a left atrial lead 620 having an atrial tip electrode 622 and an atrial ring electrode 623 implanted in the atrial appendage. Pacer/ICD 10 is also in electrical communication with the heart by way of a right ventricular lead 630 having, in this embodiment, a ventricular tip electrode 632, a right ventricular ring electrode 634, a right ventricular (RV) coil electrode 636, and a superior vena cava (SVC) coil electrode 638. Typically, the right ventricular lead 630 is transvenously inserted into the heart so as to place the RV coil electrode 636 in the right ventricular apex, and the SVC coil electrode 638 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 10 is coupled to a CS lead 624 designed for placement in the "CS region" via the CS os for positioning a distal electrode adjacent to the left ventricle and/or additional electrode(s) adjacent to the left atrium. As used herein, the phrase "CS region" refers to the venous vasculature of the left ventricle, including any portion of the CS, great cardiac vein, left marginal vein, left posterior ventricular vein, middle cardiac vein, and/or small cardiac vein or any other cardiac vein accessible by the CS. Accordingly, an exemplary CS lead 624 is designed to receive atrial and ventricular cardiac signals and to deliver left ventricular pacing therapy using at least a left ventricular tip electrode 626 and a LV ring electrode 625, left atrial pacing therapy using at least a left atrial ring electrode 627, and shocking therapy using at least a left atrial coil electrode 628. With this configuration, biventricular pacing can be performed. Although only three leads are shown in FIG. 8, it should also be understood that additional leads (with one or more pacing, sensing and/or shocking electrodes) might be used and/or additional electrodes might be provided on the leads already shown.

A simplified block diagram of internal components of pacer/ICD 10 is shown in FIG. 9. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation. The housing 640 for pacer/ICD 10, shown schematically in FIG. 9, is often referred to as the "can", "case" or "case electrode" and may be programmably selected to act as the return electrode for all "unipolar" modes. The housing 640 may further be used as a return electrode alone or in combination with one or more of the coil electrodes, 628, 636 and 638, for shocking purposes. The housing 640 further includes a connector (not shown) having a plurality of terminals, 642, 643, 644, 645, 646, 648, 652, 654, 656 and 658 (shown schematically and, for convenience, the names of the electrodes to which they are connected are shown next to the terminals). As such, to achieve right atrial sensing and pacing, the connector includes at least a right atrial tip terminal ($A_R$ TIP) 642 adapted for connection to the atrial tip electrode 622 and a right atrial ring ($A_R$ RING) electrode 643 adapted for connection to right atrial ring electrode 623. To achieve left chamber sensing, pacing and shocking, the connector includes at least a left ventricular tip terminal ($V_L$ TIP) 644, a left ventricular ring terminal ($V_L$ RING) 645, a left atrial ring terminal ($A_L$ RING) 646, and a left atrial shocking terminal ($A_L$ COIL) 648, which are adapted for connection to the left ventricular ring electrode 625, the left atrial ring electrode 627, and the left atrial coil electrode 628, respectively. To support right chamber sensing, pacing and shocking, the connector further includes a right ventricular tip terminal ($V_R$ TIP) 652, a right ventricular ring terminal ($V_R$ RING) 654, a right ventricular shocking terminal ($V_R$ COIL) 656, and an SVC shocking terminal (SVC COIL) 658, which are adapted for connection to the right ventricular tip electrode 632, right ventricular ring electrode 634, the $V_R$ coil electrode 636, and the SVC coil electrode 638, respectively.

At the core of pacer/ICD 10 is a programmable microcontroller 660, which controls the various modes of stimulation therapy. As is well known in the art, the microcontroller 660 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 660 includes the ability to process or monitor input signals (data) as controlled by a program code stored in a designated block of memory. The details of the design and operation of the microcontroller 660 are not critical to the invention. Rather, any suitable microcontroller 660 may be used that carries out the functions described herein. The use of microprocessor-based control circuits for performing timing and data analysis functions are well known in the art.

As shown in FIG. 9, an atrial pulse generator 670 and a ventricular pulse generator 672 generate pacing stimulation pulses for delivery by the right atrial lead 620, the right ventricular lead 630, and/or the CS lead 624 via an electrode configuration switch 674. It is understood that in order to provide stimulation therapy in each of the four chambers of the heart, the atrial and ventricular pulse generators, 670 and 672, may include dedicated, independent pulse generators, multiplexed pulse generators or shared pulse generators. The pulse generators, 670 and 672, are controlled by the microcontroller 660 via appropriate control signals, 676 and 678, respectively, to trigger or inhibit the stimulation pulses.

The microcontroller 660 further includes timing control circuitry (not separately shown) used to control the timing of such stimulation pulses (e.g., pacing rate, AV delay, atrial interconduction (inter-atrial) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 674 includes a plurality of switches for connecting the desired electrodes to the appropriate I/O circuits, thereby providing complete electrode programmability. Accordingly, the switch 674, in response to a control signal 680 from the microcontroller 660, determines the polarity of the stimulation pulses (e.g., unipolar, bipolar, combipolar, etc.) by selectively closing the appropriate combination of switches (not shown) as is known in the art.

Atrial sensing circuits 682 and ventricular sensing circuits 684 may also be selectively coupled to the right atrial lead 620, CS lead 624, and the right ventricular lead 630, through the switch 674 for detecting the presence of cardiac activity in each of the four chambers of the heart. Accordingly, the atrial (ATR. SENSE) and ventricular (VTR. SENSE) sensing circuits, 682 and 684, may include dedicated sense amplifiers, multiplexed amplifiers or shared amplifiers. The switch 674 determines the "sensing polarity" of the cardiac signal by selectively closing the appropriate switches, as is also known in the art. In this way, the clinician may program the sensing polarity independent of the stimulation polarity. Each sensing circuit, 682 and 684, preferably employs one or more low power, precision amplifiers with programmable gain and/or automatic gain control, bandpass filtering, and a threshold detection circuit, as known in the art, to selectively sense the cardiac signal of interest. The automatic gain control enables pacer/ICD 10 to deal effectively with the difficult problem of sensing the low amplitude signal characteristics of atrial or ventricular fibrillation. The outputs of the atrial and ventricular sensing circuits, 682 and 684, are connected to the microcontroller 660 which, in turn, are able to trigger or inhibit the atrial and ventricular pulse generators, 670 and 672, respectively, in a demand fashion in response to the absence or presence of cardiac activity in the appropriate chambers of the heart.

For arrhythmia detection, pacer/ICD 10 utilizes the atrial and ventricular sensing circuits, 682 and 684, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., AS, VS, and depolarization signals associated with fibrillation which are sometimes referred to as "F-waves" or "Fib-waves") are then classified by the microcontroller 660 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 690. The data acquisition system 690 is configured to acquire intracardiac electrogram signals, convert the raw analog data into a digital signal, and store the digital signals for later processing and/or telemetric transmission to an external device 702. The data acquisition system 690 is coupled to the right atrial lead 620, the CS lead 624, and the right ventricular lead 630 through the switch 674 to sample cardiac signals across any pair of desired electrodes. The microcontroller 660 is further coupled to a memory 694 by a suitable data/address bus 696, wherein the programmable operating parameters used by the microcontroller 660 are stored and modified, as required, in order to customize the operation of pacer/ICD 10 to suit the needs of a particular patient. Such operating parameters define, for example, the amplitude or magnitude, pulse duration, electrode polarity, for both pacing pulses and impedance detection pulses as well as pacing rate, sensitivity, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 10 may be non-invasively programmed into the memory 694 through a telemetry circuit 700 in telemetric communication with the external device 702, such as a programmer, transtelephonic transceiver or a diagnostic system analyzer. The telemetry circuit 700 is activated by the microcontroller by a control signal 706. The telemetry circuit 700 advantageously allows intracardiac electrograms and status information relating to the operation of pacer/ICD 10 (as contained in the microcontroller 660 or memory 694) to be sent to the external device 702 through an established communication link 704. Pacer/ICD 10 further includes an accelerometer or other physiologic sensor or sensors 708, sometimes referred to as a "rate-responsive" sensor because it is typically used to adjust pacing stimulation rate according to the exercise state of the patient.

However, physiological sensor(s) 708 can be equipped to sense any of a variety of cardiomechanical parameters, such as heart sounds, systemic pressure, etc. As can be appreciated, at least some these sensors may be mounted outside of the housing of the device and, in many cases, will be mounted to the leads of the device. Examples of physiological sensors that might be used with the device are described in: U.S. patent application Ser. No. 11/927,026, filed Oct. 29, 2007, of Nabutovsky et al., entitled "Systems and Methods for Exploiting Venous Blood Oxygen Saturation in combination with Hematocrit or Other Sensor Parameters for use with an Implantable Medical Device."

Moreover, the physiological sensor 708 may further be used to detect changes in cardiac output, changes in the physiological condition of the heart, or diurnal changes in activity (e.g., detecting sleep and wake states) and to detect arousal from sleep. Accordingly, the microcontroller 660 responds by adjusting the various pacing parameters (such as rate, AV delay, V-V delay, etc.) at which the atrial and ventricular pulse generators, 670 and 672, generate stimulation pulses. While shown as being included within pacer/ICD 10, it is to be understood that the physiologic sensor 708 may also be external to pacer/ICD 10, yet still be implanted within or carried by the patient. A common type of rate responsive sensor is an activity sensor incorporating an accelerometer or a piezoelectric crystal and/or a 3D-accelerometer capable of determining the posture within a given patient, which is mounted within the housing 640 of pacer/ICD 10. Other types of physiologic sensors are also known, for example, sensors that sense the oxygen content of blood, respiration rate and/or minute ventilation, pH of blood, ventricular gradient, etc., The pacer/ICD additionally includes a battery 710, which provides operating power to all of the circuits shown in FIG. 9. The battery 710 may vary depending on the capabilities of pacer/ICD 10. If the system only provides low voltage therapy, a lithium iodine or lithium copper fluoride cell typically may be utilized. For pacer/ICD 10, which employs shocking therapy, the battery 710 should be capable of operating at low current drains for long periods, and then be capable of providing high-current pulses (for capacitor charging) when the patient requires a shock pulse. The battery 710 should also have a predictable discharge characteristic so that elective replacement time can be detected. Accordingly, appropriate batteries are employed.

As further shown in FIG. 9, pacer/ICD 10 is shown as having an impedance measuring circuit 712, which is enabled by the microcontroller 660 via a control signal 714. Uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; and detecting the opening of heart valves, etc. The impedance measuring circuit 712 is advantageously coupled to the switch 774 so that any desired electrode may be used. The impedance measuring circuit 712 also detects the impedance signals discussed above to use in estimating LAP. That is, impedance measuring circuit 712 is an electrical impedance (Z) detector operative to detect an electrical impedance (Z) signal within the patient along at least one sensing vector wherein impedance is affected by cardiac pressure, but preferably over at least three vectors that form a triangle that will permit the derivation of the near-field impedance associated with each electrode individually.

In the case where pacer/ICD 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 660 further controls a shocking circuit 716 by way of a control signal 718. The shocking circuit 716 generates shocking pulses of low (up to 0.5 joules), moderate (0.5-10 joules) or high energy (11 to 40 joules or more), as controlled by the microcontroller 660. Such shocking pulses are applied to the heart of the patient through at least two shocking electrodes, and as shown in this embodiment, selected from the left atrial coil electrode 628, the RV coil electrode 636, and/or the SVC coil electrode 638. The housing 640 may act as an active electrode in combination with the RV electrode 636, or as part of a split electrical vector using the SVC coil electrode 638 or the left atrial coil electrode 628 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 7-40 joules), delivered asynchronously (since R-waves may be too disorganized), and pertaining exclusively to the treatment of fibrillation. Accordingly, the microcontroller 660 is capable of controlling the synchronous or asynchronous delivery of the shocking pulses.

Insofar as LAP estimation is concerned, the microcontroller includes an acute MR detection system 701 operative to detect acute MR within the patient. The microcontroller also includes an MR-responsive zLAP estimation system 703 operative to estimate LAP or other forms of cardiac pressure based on admittance using the techniques described above that take into account the presence or absence of acute MR. That is, the estimation system includes a non-MR zLAP estimation system 705 operative in the absence of acute MR and an acute MR zLAP estimation system 707 operative if acute MR is indicated.

Diagnostic data pertaining to zLAP and MR can be stored in memory 694. Warning and/or notification signals are generated, when appropriate, by a warning controller 709 then relayed to the bedside monitor 16 or to external programmer 702 (or other external system) via telemetry system 700. Controller 709 is also equipped to control therapy, including controlling an implantable drug pump, if one is provided, to deliver appropriate medications. Terminals for connecting the implanted warning device and the implanted drug pump to the pacer/ICD are not separately shown.

Depending upon the implementation, the various components of the microcontroller may be implemented as separate software modules or the modules may be combined to permit a single module to perform multiple functions. In addition, although shown as being components of the microcontroller, some or all of these components may be implemented separately from the microcontroller, using application specific integrated circuits (ASICs) or the like.

At least some of the techniques described herein can be performed by (or under the control of) a suitably-equipped external device. For the sake of completeness, an exemplary device programmer will now be described, which includes components for performing or controlling at least some of the functions and steps already described.

Exemplary External Programmer

Figure 10:
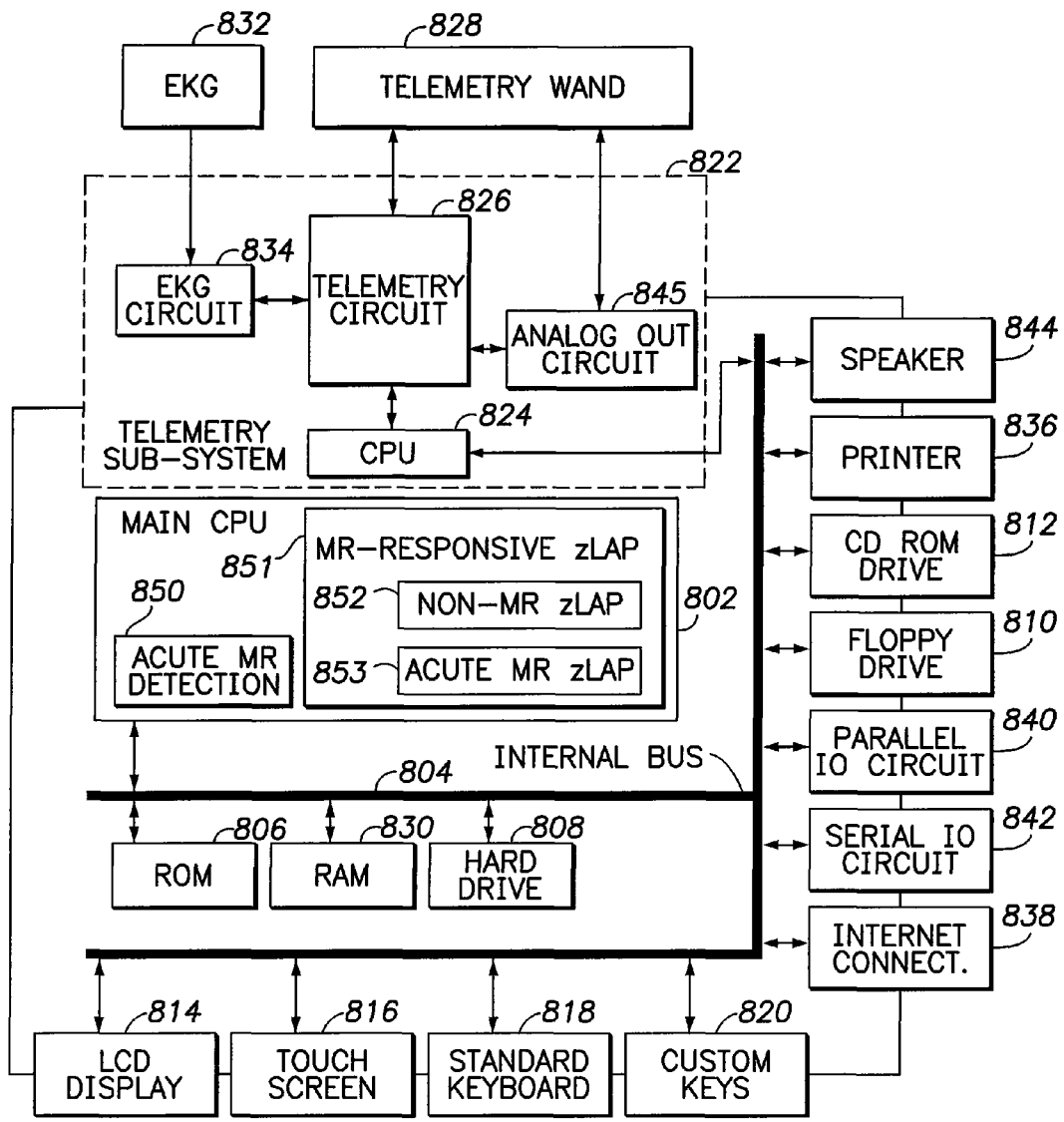
FIG. 10 is a functional block diagram illustrating components of a device programmer of FIG. 9, and in particular illustrating programmer-based zLAP estimation components that account for a possible acute MR within the patient.

FIG. 10 illustrates pertinent components of an external programmer 702 for use in programming the pacer/ICD of FIG. 9 and for performing the above-described calibration techniques. For the sake of completeness, other device programming functions are also described herein. Generally, the programmer permits a physician or other user to program the operation of the implanted device and to retrieve and display information received from the implanted device such as IEGM data and device diagnostic data. Additionally, the external programmer can be optionally equipped to receive and display electrocardiogram (EKG) data from separate external EKG leads that may be attached to the patient. Depending upon the specific programming of the external programmer, programmer 702 may also be capable of processing and analyzing data received from the implanted device and from the EKG leads to, for example, render preliminary diagnosis as to medical conditions of the patient or to the operations of the implanted device.

Now, considering the components of programmer 702, operations of the programmer are controlled by a CPU 802, which may be a generally programmable microprocessor or microcontroller or may be a dedicated processing device such as an application specific integrated circuit (ASIC) or the like. Software instructions to be performed by the CPU are accessed via an internal bus 804 from a read only memory (ROM) 806 and random access memory 830. Additional software may be accessed from a hard drive 808, floppy drive 810, and CD ROM drive 812, or other suitable permanent mass storage device. Depending upon the specific implementation, a basic input output system (BIOS) is retrieved from the ROM by CPU at power up. Based upon instructions provided in the BIOS, the CPU "boots up" the overall system in accordance with well-established computer processing techniques.

Once operating, the CPU displays a menu of programming options to the user via an LCD display 814 or other suitable computer display device. To this end, the CPU may, for example, display a menu of specific programmable parameters of the implanted device to be programmed or may display a menu of types of diagnostic data to be retrieved and displayed. In response thereto, the physician enters various commands via either a touch screen 816 overlaid on the LCD display or through a standard keyboard 818 supplemented by additional custom keys 820, such as an emergency VVI (EVVI) key. The EVVI key sets the implanted device to a safe VVI mode with high pacing outputs. This ensures life sustaining pacing operation in nearly all situations, but by no means is it desirable to leave the implantable device in the EVVI mode at all times.

Once all pacing leads are mounted and the pacing device is implanted, the various parameters are programmed. Typically, the physician initially controls the programmer 702 to retrieve data stored within any implanted devices and to also retrieve EKG data from EKG leads, if any, coupled to the patient. To this end, CPU 802 transmits appropriate signals to a telemetry subsystem 822, which provides components for directly interfacing with the implanted devices, and the EKG leads. Telemetry subsystem 822 includes its own separate CPU 824 for coordinating the operations of the telemetry subsystem. Main CPU 802 of programmer communicates with telemetry subsystem CPU 824 via internal bus 804. Telemetry subsystem additionally includes a telemetry circuit 826 connected to telemetry wand 828, which, in turn, receives and transmits signals electromagnetically from a telemetry unit of the implanted device. The telemetry wand is placed over the chest of the patient near the implanted device to permit reliable transmission of data between the telemetry wand and the implanted device. Herein, the telemetry subsystem is shown as also including an EKG circuit 834 for receiving surface EKG signals from a surface EKG system 832. In other implementations, the EKG circuit is not regarded as a portion of the telemetry subsystem but is regarded as a separate component.

Typically, at the beginning of the programming session, the external programming device controls the implanted devices via appropriate signals generated by the telemetry wand to output all previously recorded patient and device diagnostic information. Patient diagnostic information includes, for example, recorded IEGM data and statistical patient data such as the percentage of paced versus sensed heartbeats. Device diagnostic data includes, for example, information representative of the operation of the implanted device such as lead impedances, battery voltages, battery recommended replacement time (RRT) information and the like. Data retrieved from the pacer/ICD also includes the data stored within the recalibration database of the pacer/ICD (assuming the pacer/ICD is equipped to store that data.) Data retrieved from the implanted devices is stored by external programmer 702 either within a random access memory (RAM) 830, hard drive 808 or within a floppy diskette placed within floppy drive 810. Additionally, or in the alternative, data may be permanently or semi-permanently stored within a compact disk (CD) or other digital media disk, if the overall system is configured with a drive for recording data onto digital media disks, such as a write once read many (WORM) drive or a USB thumb drive.

Once all patient and device diagnostic data previously stored within the implanted devices is transferred to programmer 702, the implanted devices may be further controlled to transmit additional data in real time as it is detected by the implanted devices, such as additional IEGM data, lead impedance data, and the like. Additionally, or in the alternative, telemetry subsystem 822 receives EKG signals from EKG leads 832 via an EKG processing circuit 834. As with data retrieved from the implanted device itself, signals received from the EKG leads are stored within one or more of the storage devices of the external programmer. Typically, EKG leads output analog electrical signals representative of the EKG. Accordingly, EKG circuit 834 includes analog to digital conversion circuitry for converting the signals to digital data appropriate for further processing within the programmer. Depending upon the implementation, the EKG circuit may be configured to convert the analog signals into event record data for ease of processing along with the event record data retrieved from the implanted device. Typically, signals received from the EKG leads are received and processed in real time.

Thus, the programmer receives data both from the implanted devices and from optional external EKG leads. Data retrieved from the implanted devices includes parameters representative of the current programming state of the implanted devices. Under the control of the physician, the external programmer displays the current programmable parameters and permits the physician to reprogram the parameters. To this end, the physician enters appropriate commands via any of the aforementioned input devices and, under control of CPU 802, the programming commands are converted to specific programmable parameters for transmission to the implanted devices via telemetry wand 828 to thereby reprogram the implanted devices. Prior to reprogramming specific parameters, the physician may control the external programmer to display any or all of the data retrieved from the implanted devices or from the EKG leads, including displays of EKGs, IEGMs, and statistical patient information.

Any or all of the information displayed by programmer may also be printed using a printer 836.

Additionally, CPU 802 can include an acute MR detection system 850 operative to detect acute MR within the patient based on data measured within the patient by the implantable device and sent to the external programmer. The CPU also includes an MR-responsive zLAP controller 851 having a non-MR zLAP estimation system 852 operative to estimate LAP based on admittance signals or other data (measured within the patient by the implantable device and sent to the external programmer) using formulae or models appropriate for use in the absence of acute MR and an acute MR zLAP estimation system 853 operative to estimate LAP based on admittance signals or other data (again measured within the patient by the implantable device and sent to the external programmer) using formulae or models appropriate for use in the presence of acute MR.

Programmer/monitor 702 also includes a modem or other internet connection 838 to permit direct transmission of data to other programmers via the public switched telephone network (PSTN) or other interconnection line, such as a T1 line or fiber optic cable. Depending upon the implementation, the modem may be connected directly to internal bus 804 may be connected to the internal bus via either a parallel port 840 or a serial port 842. Other peripheral devices may be connected to the external programmer via parallel port 840 or a serial port 842 as well. Although one of each is shown, a plurality of input output (IO) ports might be provided. A speaker 844 is included for providing audible tones to the user, such as a warning beep in the event improper input is provided by the physician. Telemetry subsystem 822 additionally includes an analog output circuit 845 for controlling the transmission of analog output signals, such as IEGM signals output to an EKG machine or chart recorder.

With the programmer configured as shown, a physician or other user operating the external programmer is capable of retrieving, processing and displaying a wide range of information received from the implanted devices and to reprogram the implanted device if needed. The descriptions provided herein with respect to FIG. 10 are intended merely to provide an overview of the operation of programmer and are not intended to describe in detail every feature of the hardware and software of the programmer and is not intended to provide an exhaustive list of the functions performed by the programmer.

Depending upon the implementation, the various components of the microcontroller may be implemented as separate software modules or the modules may be combined to permit a single module to perform multiple functions. In addition, although shown as being components of the microcontroller, some or all of these components may be implemented separately from the microcontroller, using ASICs or the like.

In general, while the invention has been described with reference to particular embodiments, modifications can be made thereto without departing from the spirit and scope of the invention. Note also that the term "including" as used herein is intended to be inclusive, i.e. "including but not limited to."

What is claimed is:

1. A method for estimating cardiac pressure within a patient for use with an implantable medical device, the method comprising:
   detecting an indication of acute mitral valve regurgitation (MR), if occurring within the patient;
   applying an electrical field to tissues of the patient including cardiac tissues and measuring an electrical parameter influenced by the applied electrical field and affected by cardiac pressure; and estimating cardiac pressure within the patient based on the electrical parameter and the indication of acute MR.

2. The method of claim 1 wherein applying an electrical field to tissues of the patient includes applying a detection pulse from which one or more of impedance (Z), admittance (Y) and conductance (G) can be measured.

3. The method of claim 1 wherein measuring the electrical parameter includes:

measuring one or more of impedance (Z), admittance (Y) and conductance (G) signal within the patient along one or more sensing vectors passing through cardiac tissue; and deriving the electrical parameter from the detected signal.

4. The method of claim 1 wherein estimating cardiac pressure based on the electrical parameter is performed using one or more of a linear correlation, an exponential correlation and a polynomial correlation.

5. The method of claim 4 wherein estimating cardiac pressure includes calculating Cardiac Pressure=Parameter* Slope+Baseline if acute MR is not indicated, wherein Slope and Baseline are conversion factors representative of a linear correlation between the measured electrical parameter and the cardiac pressure; and calculating Cardiac Pressure=Parameter* Slope+Baseline+MR Correction if acute MR is indicated, wherein MR Correction is a correction factor for compensating for the affects of MR on the estimation.

6. The method of claim 5 wherein the MR Correction term is a constant.

7. The method of claim 5 wherein detecting the indication of MR includes detecting the degree of MR and wherein the MR correction term is adjusted based on the degree of MR.

8. The method of claim 5 further including detecting left ventricular (LV) volume and wherein the MR correction term is adjusted based on LV volume.

9. The method of claim 1 for use with a device equipped to measure heart sounds and wherein detecting the indication of acute MR within the patient includes:

detecting heart sounds within the patient; and detecting the presence of acute MR based on the heart sounds.

10. The method of claim 9 further including assessing the severity of acute MR based on the heart sounds.

11. The method of claim 1 for use with a device equipped to measure admittance associated with electrodes mounted on a LV-sided and a RV-sided pacing leads and wherein the indication of acute MR is detected based on the admittance values associated with the LV-sided and RV-sided electrodes.

12. The method of claim 1 for use with a device equipped to measure cardiogenic impedance waveforms and wherein detecting the indication of acute MR within the patient includes:

detecting a cardiogenic impedance waveform along vectors affected by acute MR; and detecting acute MR based on changes in the cardiogenic impedance waveform.

13. The method of claim 1 for use with a device equipped to measure systemic blood pressure and wherein detecting the indication of acute MR within the patient includes:

detecting systemic blood pressure associated with an increase in afterload within the patient; and detecting the presence of acute MR based on systemic blood pressure.

14. The method of claim 1 for use with a device equipped with an activity sensor and wherein the method includes the additional steps of:

detecting patient activity within the patient using the sensor; and detecting the indication of acute MR based on activity sensor signal associated with increased afterload.

15. The method of claim 1 for use with a device equipped to measure intracardiac electrograms (IEGM) and wherein the method includes the additional steps of:

detecting ST segments within IEGMs within the patient; and detecting the indication of acute MR based on changes in ST segment elevation.

16. The method of claim 1 for use with a device equipped to measure the IEGM and wherein the method includes the additional steps of:

determining the relative timing of the atrial and ventricular contractions; and detecting the indication of acute MR based on the relative time of the atrial and ventricular contractions.

17. The method of claim 1 further including generating warning signals based on the estimate of cardiac pressure.

18. The method of claim 1 further including controlling therapy based on the estimate of cardiac pressure.

19. A system for use with an implantable medical device for implant within a patient, the system comprising:

an acute mitral valve regurgitation (MR) detection system operative to detect an indication of acute MR, if occurring within the patient;

an electrical field generator operative to apply an electric field to tissues of the patient including cardiac tissues and further operative to measure an electrical parameter influenced by the applied electrical field and affected by cardiac pressure; and a cardiac pressure estimation system operative to estimate cardiac pressure within the patient based on the electrical parameter and the indication of acute MR.

20. A system for use with an implantable medical device for implant within a patient, the system comprising:

means for detecting an indication of acute mitral valve regurgitation (MR), if occurring within the patient;

means for applying an electrical field to tissues of the patient including cardiac tissues and measuring an electrical parameter influenced by the applied electrical field and affected by cardiac pressure; and means for estimating cardiac pressure within the patient based on the electrical parameter and the indication of acute MR.

* * * * *